United States Patent
Otsu et al.

(10) Patent No.: US 8,192,847 B2
(45) Date of Patent: *Jun. 5, 2012

(54) ORGANIC ELECTROLUMINESCENT DEVICE MATERIAL, ORGANIC ELECTROLUMINESCENT DEVICE, DISPLAY AND ILLUMINATING DEVICE

(75) Inventors: Shinya Otsu, Tokyo (JP); Eisaku Katoh, Tokyo (JP)

(73) Assignee: Konica Minolta Holdings, Inc., Tokyo (JP)

( * ) Notice: Subject to any disclaimer, the term of this patent is extended or adjusted under 35 U.S.C. 154(b) by 716 days.

This patent is subject to a terminal disclaimer.

(21) Appl. No.: 12/300,814

(22) PCT Filed: May 16, 2007

(86) PCT No.: PCT/JP2007/060029
§ 371 (c)(1),
(2), (4) Date: Nov. 14, 2008

(87) PCT Pub. No.: WO2007/132886
PCT Pub. Date: Nov. 22, 2007

(65) Prior Publication Data
US 2009/0167165 A1 Jul. 2, 2009

(30) Foreign Application Priority Data
May 17, 2006 (JP) .................................. 2006-137500

(51) Int. Cl.
*H01L 51/54* (2006.01)
*C09K 11/00* (2006.01)
(52) U.S. Cl. ........ 428/690; 428/917; 313/504; 313/506; 252/301.16; 257/40; 257/103; 257/E51.051; 548/440; 549/43; 549/460
(58) Field of Classification Search ........... 257/E51.051; 548/108, 440; 549/43, 460
See application file for complete search history.

(56) References Cited

U.S. PATENT DOCUMENTS

| | | | |
|---|---|---|---|
| 2002/0079835 A1* | 6/2002 | Lee ................................ | 313/506 |
| 2002/0086180 A1* | 7/2002 | Seo et al. ....................... | 428/690 |
| 2004/0110031 A1* | 6/2004 | Fukuda et al. ................. | 428/690 |
| 2006/0251923 A1* | 11/2006 | Lin et al. ........................ | 428/690 |
| 2006/0280966 A1* | 12/2006 | Otsu et al. ...................... | 428/690 |
| 2008/0054799 A1* | 3/2008 | Satou ............................. | 313/504 |

FOREIGN PATENT DOCUMENTS

| | | |
|---|---|---|
| JP | 2004171808 | 6/2004 |
| JP | 2005228737 | 8/2005 |
| JP | 200669962 | 3/2006 |
| JP | 2006303470 | 11/2006 |

* cited by examiner

*Primary Examiner* — Jennifer Chriss
*Assistant Examiner* — Michael H Wilson
(74) *Attorney, Agent, or Firm* — Lucas & Mercanti, LLP

(57) ABSTRACT

Disclosed is a novel organic EL device material. Also disclosed are an organic EL device, an illuminating device and a display each having high emission efficiency and long emission lifetime, which are obtained by employing the organic EL device material.

19 Claims, 1 Drawing Sheet

LIGHT

LIGHT

ORGANIC ELECTROLUMINESCENT DEVICE MATERIAL, ORGANIC ELECTROLUMINESCENT DEVICE, DISPLAY AND ILLUMINATING DEVICE

This is a U.S. National Phase Application under 35 U.S.C. 371 of International Application PCT/JP2007/060029, filed on May 16, 2007, which claims the priority of Japanese Application No. 2006-137500, filed May 17, 2006, the entire content of both Applications are hereby incorporated by reference.

FIELD OF THE INVENTION

This invention relates to an organic electroluminescent device material, an organic electroluminescent device, a display and an illuminating device.

TECHNICAL BACKGROUND

As an emission type electronic displaying device, there is an electroluminescent device (hereinafter referred to as ELD). As devices constituting the ELD, there are mentioned an inorganic electroluminescent device and an organic electroluminescent device (hereinafter referred to as organic EL device). The inorganic electroluminescent device has been used for a plane-shaped light source, but a high voltage alternating current has been required to drive the device. An organic EL device has a structure in which a light emission layer containing a light emission compound is arranged between a cathode and an anode, and an electron and a hole were injected into the light emission layer and recombined to form an exciton. The device emits light, utilizing light (fluorescent light or phosphorescent light) generated by inactivation of the exciton, and the device can emit light by applying a relatively low voltage of from several volts to several decade volts. The device has a wide viewing angle and a high visuality since the device is of self light emission type Further, the device is a thin, complete solid device, and therefore, the device is noted from the viewpoint of space saving and portability.

However, development of an organic EL device for practical use is required which efficiently emits light with high luminance at a lower power.

High emission luminance and long lifetime is attained in Patent No. Japanese Patent No. 3093796 by doping a slight amount of a fluorescent compound in stilbene derivatives, distyrylarylene derivatives or tristyrylarylene derivatives.

A device is disclosed in Japanese Patent O.P.I. Publication No. 63-264692, which comprises an organic light emission layer containing an 8-hydroxyquinoline aluminum complex as a host compound doped with a slight amount of a fluorescent compound, and a device is disclosed in Japanese Patent O.P.I. Publication No. 3-255190, which comprises an organic light emission layer containing an 8-hydroxyquinoline aluminum complex as a host compound doped with a quinacridone type dye.

When light emitted through excited singlet state is used as in the above, the upper limit of the external quantum efficiency ($\eta$ext) is considered to be at most 5%, as the generation ratio of singlet excited species to triplet excited species is 1:3, that is, the generation probability of excited species capable of emitting light is 25%, and further, external light emission efficiency is 20%.

Since an organic EL device, employing phosphorescence through the excited triplet, was reported by Prinston University (see M. A. Baldo et al., Nature, 395, p 151-154 (1998)), study on materials emitting phosphorescence at room temperature has been actively made.

For example, such an organic EL device is disclosed in M. A. Baldo et al., Nature, 403, 17, p. 750-753 (2000) or U.S. Pat. No. 6,097,147.

As the upper limit of the internal quantum efficiency of the excited triplet is 100%, the light emission efficiency of the exited triplet is theoretically four times that of the excited singlet. Such an organic EL device has possibility that exhibits the same performance as a cold cathode tube, and its application to illumination is watched.

Many compounds, mainly heavy metal complexes such as iridium complexes is synthesized and studied in for example, S. Lamansky et al., J. Am. Chem. Soc., 123, 4304 (2001).

An example employing tris(2-phenylpyridine)iridium as a dopant is studied in M. A. Baldo et al., Nature, 403, 17, p. 750-753 (2000) above.

Further, M. E. Tompson et. al. studies an example, employing as a dopant $L_2Ir$ (acac) such as $(ppy)_2Ir$ (acac) in The $10^{th}$ International Workshop on Inorganic and Organic Electroluminescence (EL' 00, Hamamatsu), and Moon-Jae Youn. Og, Tetsuo Tsutsui et. al. an example employing as a dopant tris(2-p-tolylpyridine)iridium $\{Ir(ptpy)_3\}$ or tris(benzo-[h]-quinoline)iridium $\{Ir(bzq)_3\}$ in The $10^{th}$ International Workshop on Inorganic and Organic Electroluminescence (EL' 00, Hamamatsu). (These metal complexes are generally called orthometalated iridium complexes.)

Attempt for preparing a device employing various iridium complexes is made in S. Lamansky et al., J. Am. Chem. Soc., 123, 4304 (2001) above.

Orthometalated complexes in which iridium as a center metal is replaced with platinum are also watched. Regarding these complexes, there are known many kinds of complexes having characteristics in the ligands (see for example, Patent Document Nos. 1 through 5 below)

As host compounds of these phosphorescence emitting dopants, carbazole derivatives represented by CBP or m-CP are well known. There are well known m-CP or its derivatives as a host emitting a blue light, however, these compounds do not provide satisfactory efficiency or lifetime (see for example, Patent Document Nos. 6 and 7 below), Patent document 1: Japanese Patent O.P.I. Publication No. 2002-332291
Patent document 2: Japanese Patent O.P.I. Publication No. 2002-332292
Patent document 3: Japanese Patent O.P.I. Publication No 2002-338588
Patent document 4: Japanese Patent O.P.I. Publication No. 2002-226495
Patent document 5: Japanese Patent O.P.I. Publication No. 2002-234894
Patent document 6: WO 03/080760
Patent document 7: WO 04/074399

DISCLOSURE OF THE INVENTION

Problems to be Solved by the Invention

The present invention has been made in view of the above. An object of the invention is to provide a novel organic EL device material and to provide an organic EL device, an illuminating device and a display each having high emission efficiency and long emission lifetime, which are obtained by employing the organic EL device material.

Means for Solving the Above Problems

The above object of the invention can be attained by the following constitutions 1 through 14:

1. An organic electroluminescent device comprising a substrate, and provided thereon, an anode and a cathode, at least one organic layer being provided between the anode and the cathode, characterized in that the at least one organic layer contains a compound represented by formula (1),

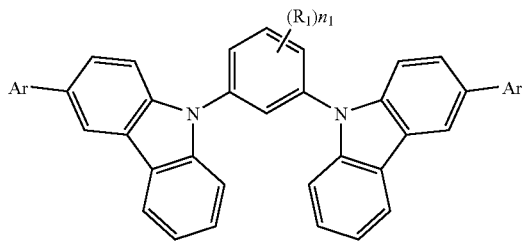

Formula (1)

wherein $R_1$ represents a hydrogen atom or a substituent; Ar represents an aromatic hydrocarbon group or an aromatic heterocyclic group; and $n_1$ represents an integer of from 0 to 4.

2. The organic electroluminescent device of item 1 above, characterized in that Ar represents an aromatic heterocyclic group.

3. The organic electroluminescent device of item 1 or 2 above, characterized in that the at least one organic layer contains a compound represented by formula (2),

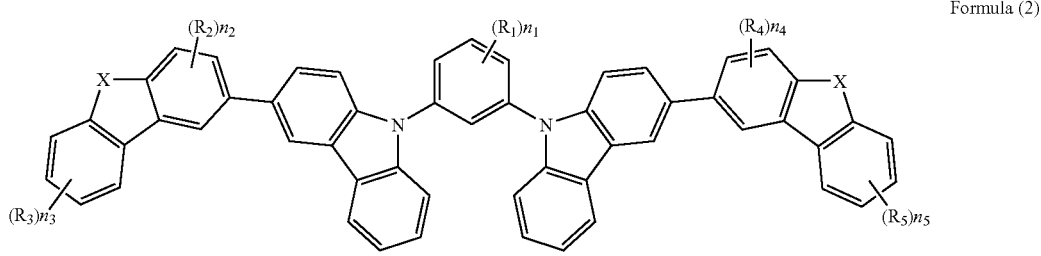

Formula (2)

wherein $R_1$ represents a hydrogen atom or a substituent; X represents O, S or —N(Ra)— (in which Ra represents a hydrogen atom, an alkyl group, an alkenyl group, an alkinyl group, or a cycloalkyl group); $R_2$ through $R_5$ independently represent a hydrogen atom or a substituent; $n_1$, $n_3$ and $n_5$ independently represent an integer of from 0 to 4; and $n_2$ and $n_4$ independently represent an integer of from 0 to 3.

4. The organic electroluminescent device of item 3 above, characterized in that X in formula (2) represents O or S.

5. The organic electroluminescent device of any one of items 1 through 4 above, characterized in that the organic layer comprises at least one light emission layer and the light emission layer contains a compound represented by formula (1) or (2).

6. The organic electroluminescent device of any one of items 1 through 5 above, characterized in that the organic layer comprises at least one electron inhibiting layer and the electron inhibiting layer contains a compound represented by formula (1) or (2).

7. The organic electroluminescent device of any one of items 1 through 6 above, characterized in that the organic layer comprises at least one hole inhibiting layer and the hole inhibiting layer contains a compound represented by formula (1) or (2).

8. The organic electroluminescent device of any one of items 5 through 7 above, characterized in that the light emission layer contains a phosphorescence emission dopant.

9. The organic electroluminescent device of item 8 above, characterized in that the phosphorescence emission dopant has a 0-0 band of not more than 485 nm.

10. The organic electroluminescent device of any one of items 1 through 9 above, characterized in that the organic electroluminescent device emits a white light.

11. A display comprising the organic electroluminescent device of any one of items 1 through 10 above.

12. An illuminating device comprising the organic electroluminescent device of any one of items 1 through 10 above.

13. A display comprising the illuminating device of item 12 above and a liquid crystal device as a displaying means.

14. An organic electroluminescent device material comprising a compound represented by formula (1) or (2) above.

EFFECTS OF THE INVENTION

The present invention can provide an organic EL device material and provide an organic EL device, an illuminating device and a display each having high emission efficiency and long lifetime (long emission lifetime), which are obtained by employing the organic EL device material.

EXPLANATION OF SYMBOLS

Figure 1:
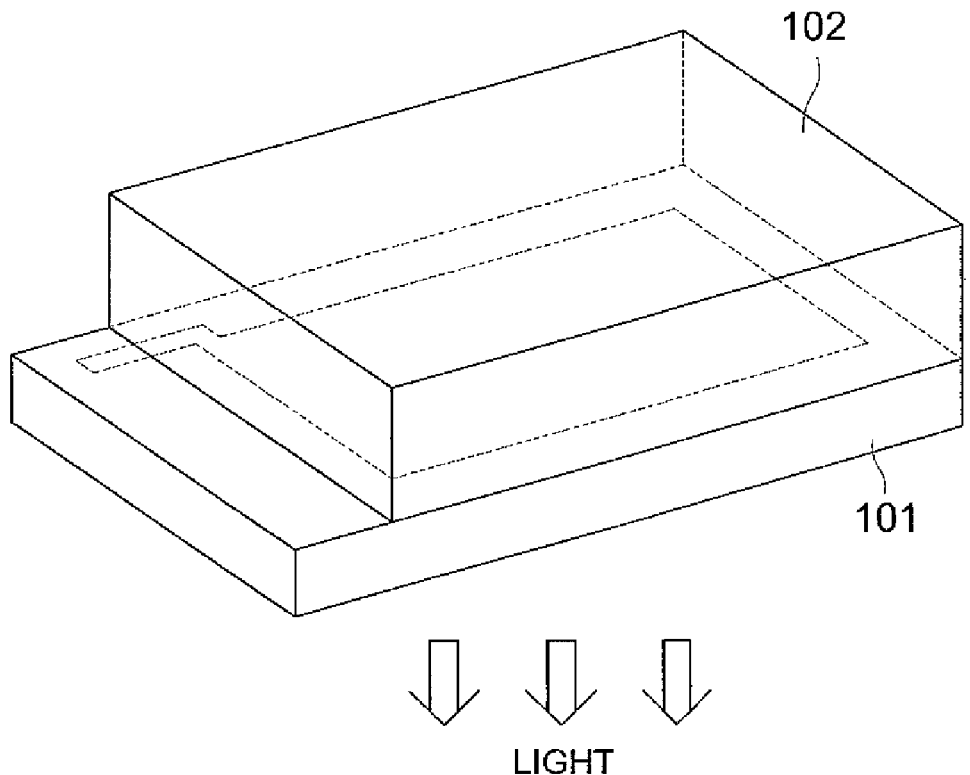
FIG. 1 is a schematic drawing of an illuminating device.

101. Organic EL device
102. Glass Cover
105. Cathode
106. Organic EL layer
107. Glass substrate with transparent electrode
108. Nitrogen gas
109. Water trapping agent

PREFERRED EMBODIMENT OF THE INVENTION

The organic EL device of the invention can attain high emission efficiency and long emission lifetime, employing a novel organic EL device material represented by formula (1) or (2).

<<Organic EL Device Material>>

The organic EL device material of the invention will be explained below.

The organic EL device material of the invention is a novel organic EL device material comprising a compound represented by formula (1) or (2) above. The content of the compound represented by formula (1) or (2) above in the organic EL device material is preferably at least 50% by weight, and may be 100% by weight.

<<Compound Represented by Formula (1)>>

In above formula (1), examples of the substituents represented by $R_1$ include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); an cycloalkyl group (for example, a cyclopentyl group and a cyclohexyl group); an alkenyl group (for example, a vinyl group and a allyl group); an alkynyl group (for example, an ethynyl group and a propargyl group); an aromatic hydrocarbon group (also referred to as aromatic carbon ring group or aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, and a biphenyl group); an aromatic heterocyclic group (for example, a pyridyl group, a pyrimidinyl group, a furyl group, a pyrrolyl group, an imidazolyl group, a benzimidazolyl group, a pyrazolyl group, a pyrazinyl group, a triazolyl group (foe example, a 1,2,4-triazole-1-yl group or a 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (in which one of the carbon atoms constituting the carboline ring of the carbolinyl group is substituted with a nitrogen atom), a quinoxalinyl group, a pyridazinyl group, a triazinyl group, a quinazolinyl group or a phthalazinyl group group); a heterocyclic group (for example, a pyrrolidyl group, an imidazolidyl group, a morpholyl group or an oxazolidyl group); an alkoxy group (for example, a methoxy group, an ethoxy group, a propyloxy group, a pentyloxy group, a hexyloxy group, an octyloxy group, and a dodecyloxy group); a cycloalkoxy group (for example, a cyclopentyloxy group and a cyclohexyloxy group), an aryloxy group (for example, a phenoxy group and a naphthyloxy group), an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group), an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a2-ethylhexylaminocarbonyl group, a dodecylaminocarbonyl group, a phenylaminocarbonyl group, a naphthylaminocarbonyl group, and a 2-puridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsulfinyl group, a butylsulfonyl group, a cyclohexylsulfinyl group, a 2-ethylhexylsulfinyl group, a dodecylsulfinyl group, a phenylsulfonyl group, a naphthylsulfinyl group, and a 2-pyridylsulfinyl group); an alkylsulfonyl group (for example, a methylsulfonyl group and an ethylsulfonyl group, a butylsulfonyl group, a cyclohexylsulfonyl group, a 2-ethylhexylsulfonyl group, and a dodecyl sulfonyl group); an arylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a 2-ethylhexylamino group, a dodecylamino group, an anilino group, a naphthylamino group, and a 2-pyridylamino group); a cyano group; an nitro group; a hydroxyl group, a mercapto group; and a silyl group (for example, a trimethylsilyl group, a triisopropylsilyl group, a triphenylsilyl group, and a phenyldiethylsilyl group).

In formula (1), examples of the aromatic hydrocarbon group represented by Ar are the same as those denoted in the aromatic hydrocarbon group of $R_1$ of formula (1).

In formula (1), examples of the aromatic heterocyclic group represented by Ar are the same as those denoted in the aromatic heterocyclic group of $R_1$ of formula (1).

In formula (1), Ar is preferably the aromatic heterocyclic group.

<<Compound Represented by Formula (2)>>

A compound represented by formula (2) in the organic EL device material of the invention will be explained below.

In formula (2), the substituents represented by $R_1$ are the same as those denoted in the substituents represented by $R_1$ in formula (1).

In formula (2), when X is —N(Ra)—, examples of the alkyl group represented by Ra include a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group, and these may have further a substituent.

In formula (2), when X is —N(Ra)—, examples of the alkenyl group represented by Ra include a vinyl group, an allyl group, a propyl group, an isopropyl group, a tert-butyl group, a pentyl group, a hexyl group, an octyl group, a dodecyl group, a tridecyl group, a tetradecyl group, and a pentadecyl group, and these may have further a substituent.

In formula (2), when X is —N(Ra)—, examples of the alkinyl group represented by Ra include an ethynyl group and an propargyl group, and these may have further a substituent;

In formula (2), when X is —N(Ra)—, examples of the cycloalkyl group represented by Ra include a cyclopentyl group and a cyclohexyl group, and these may have further a substituent.

Next, examples of a compound represented by formula (1) or (2) regarding the organic EL device material of the invention will be listed below, but the invention is not specifically limited thereto.

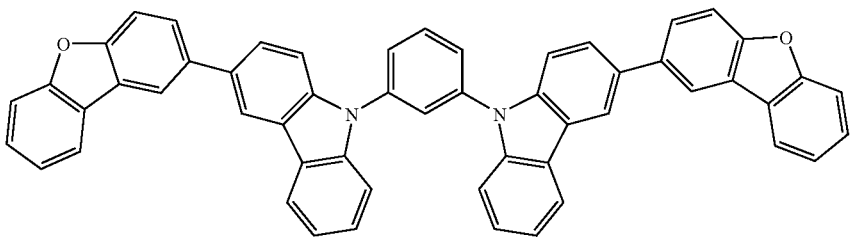

H-1

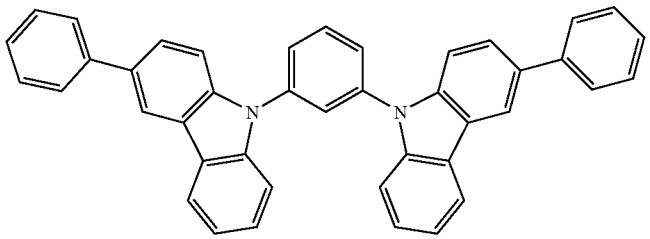

H-2

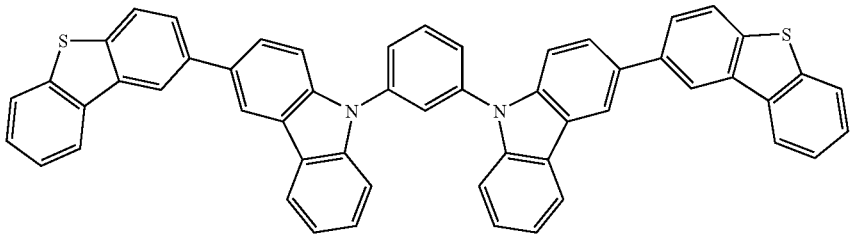

H-3

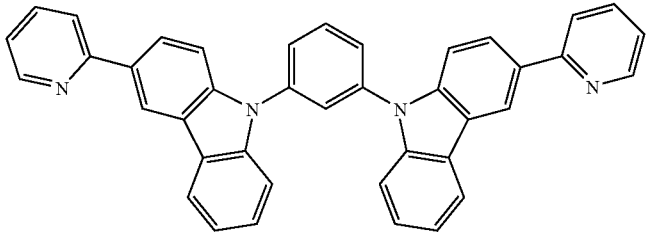

H-4

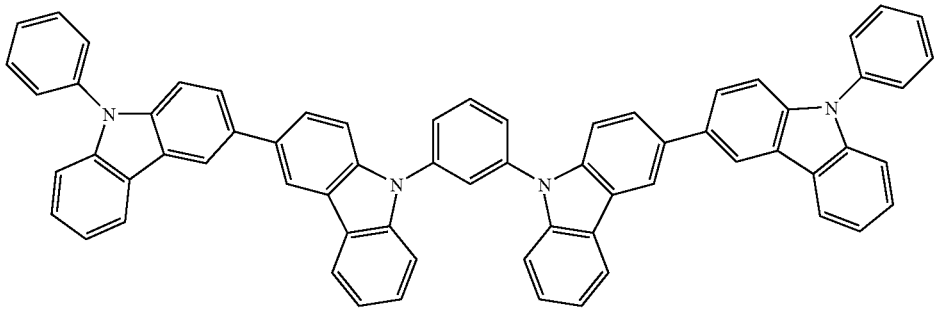

H-5

-continued
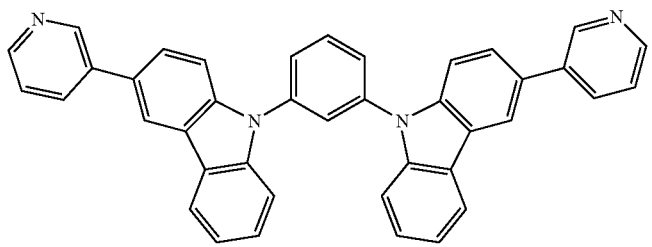
H-6
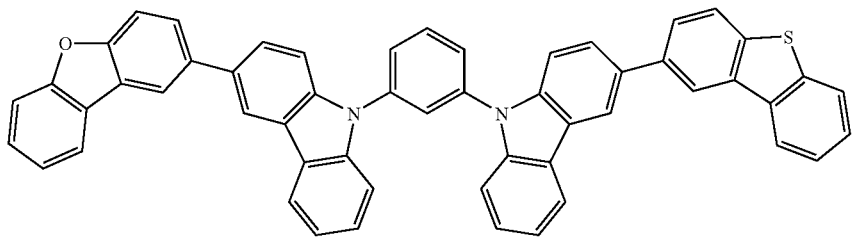
H-7
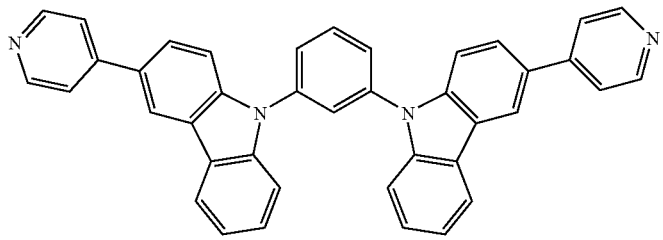
H-8
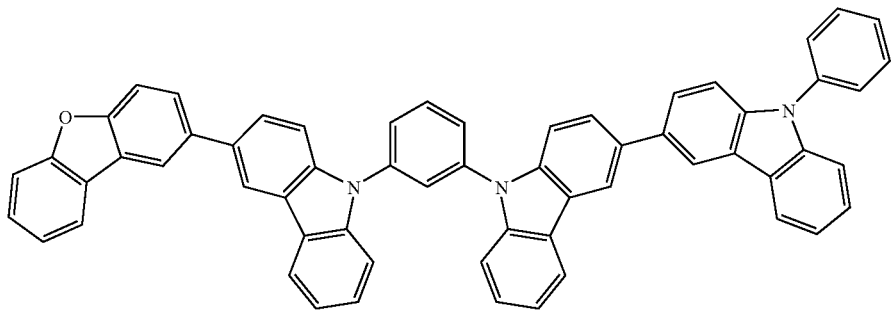
H-9
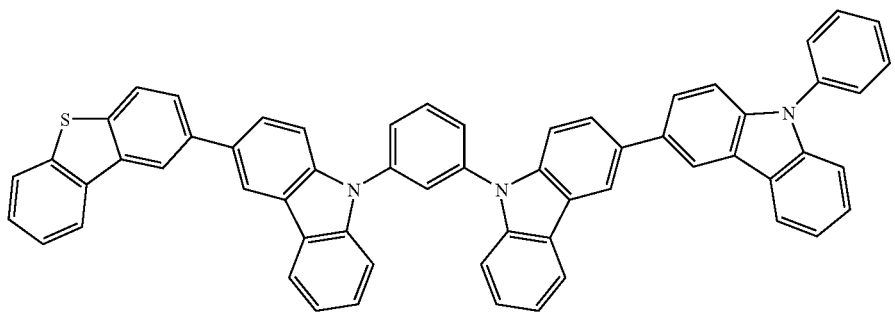
H-10

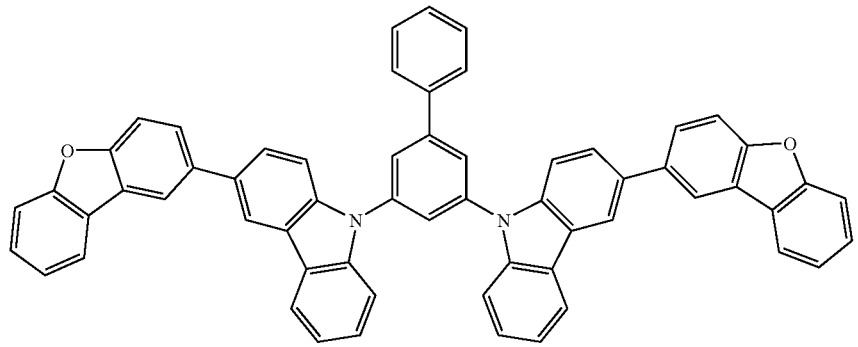
H-11
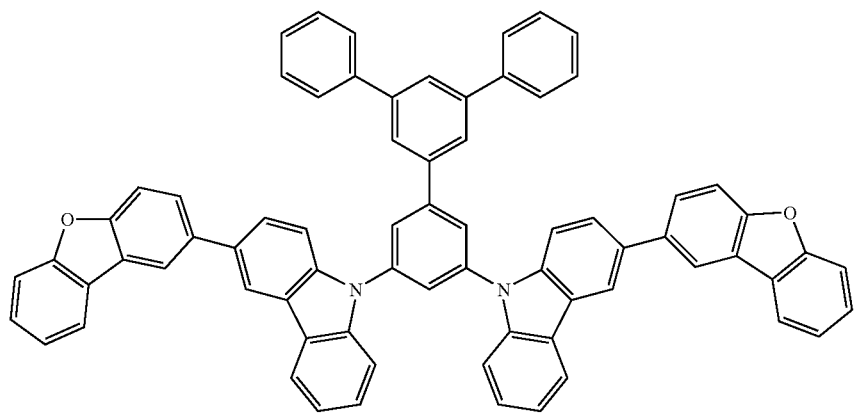
H-12
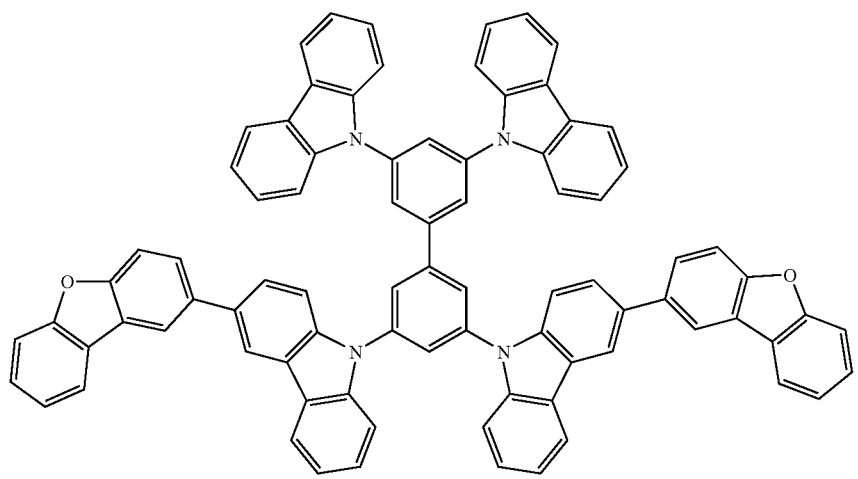
H-13

-continued
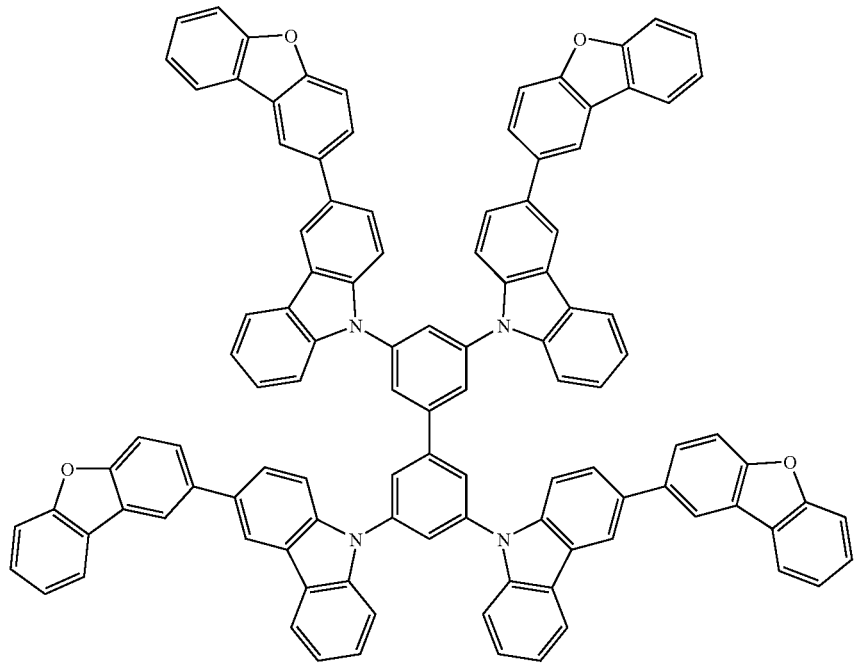
H-14
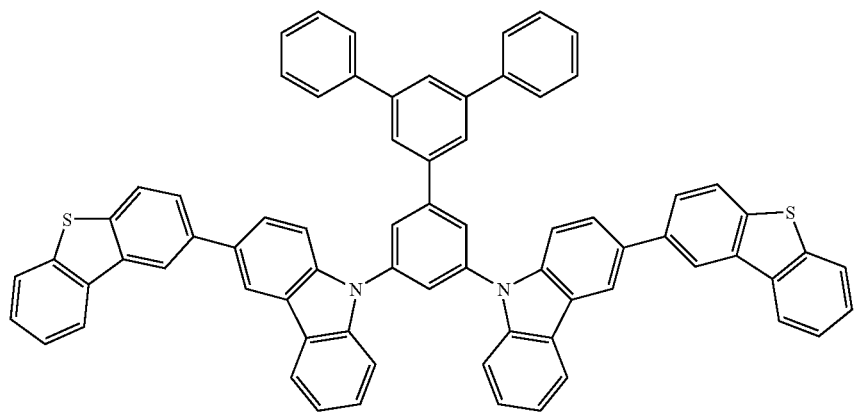
H-15
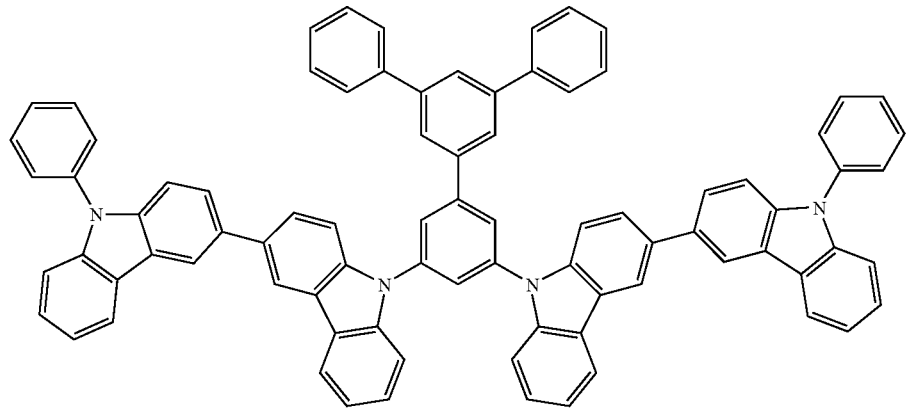
H-16

-continued

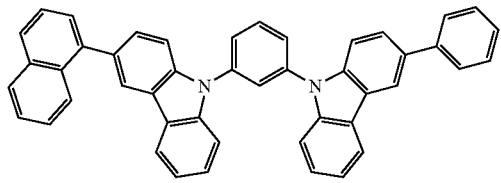
H-17

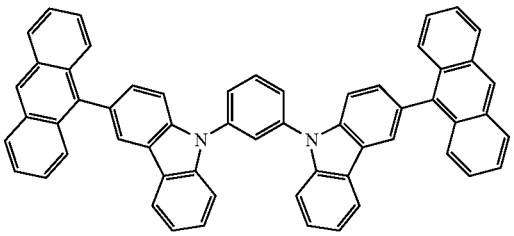
H-18

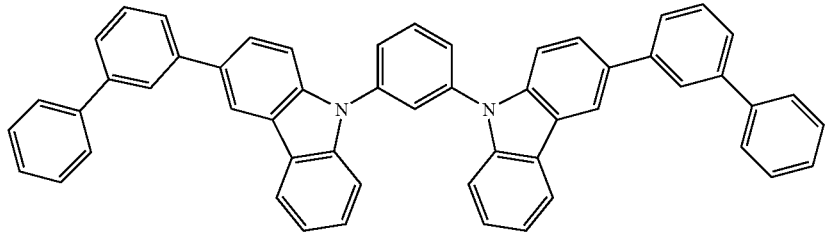
H-19

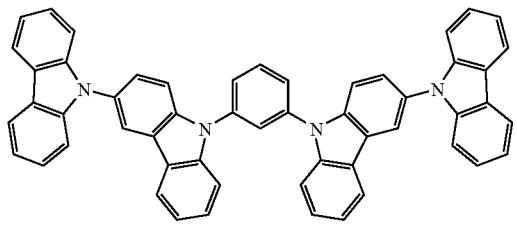
H-20

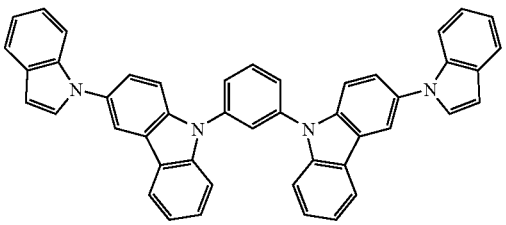
H-21

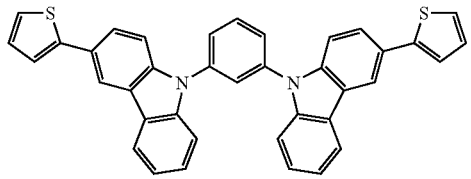
H-22

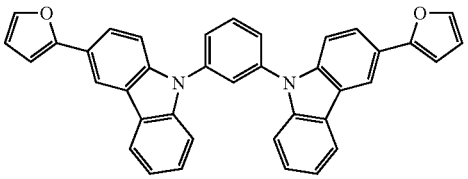
H-23

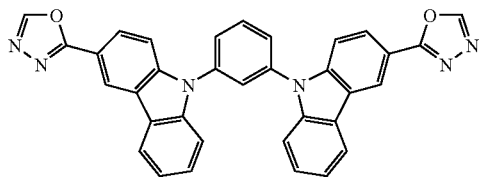
H-24

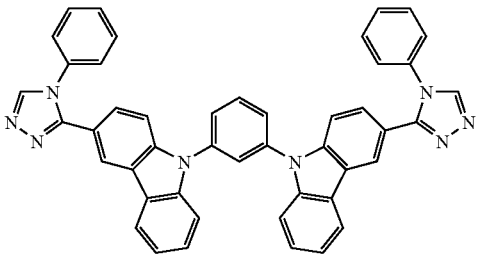
H-25

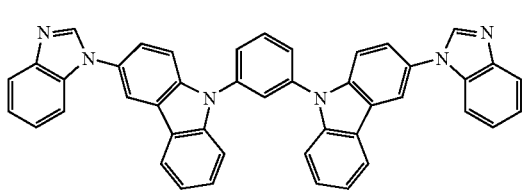
H-26

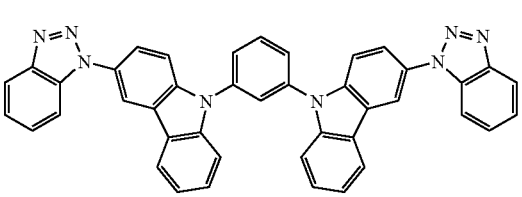
H-27

The compounds represented by formula (1) or (2) can be synthesized according to a synthetic method well known in the art (for example, a synthetic method disclosed in known documents in which a host compound described later is described).

<<Constituent Layer of Organic EL Device>>

The constituent layer of the organic EL device of the invention will be explained below. In the invention, Preferred examples of the constituent layer of the organic EL device of the invention will be shown below, but the invention is not limited thereto.

(i): Anode/Light emission layer/Electron transporting layer/Cathode (ii): Anode/Hole transporting layer/Light emission layer/Electron transporting layer/Cathode (iii): Anode/Hole transporting layer/Light emission layer/Hole blocking layer/Electron transporting layer/Cathode (iv): Anode/Hole transporting layer/Light emission layer/Hole blocking layer/Electron transporting layer/Cathode buffering layer/Cathode (v): Anode/Anode buffering layer/Hole transporting layer/Light emission layer/Hole blocking layer/Electron transporting layer/Cathode buffering layer/Cathode In the organic EL device of the invention, a blue emission layer has an emission maximum in the range of from preferably 430 to 480 nm, a green emission layer has an emission maximum in the range of from preferably 510 to 550 nm, and a red emission layer has an emission maximum in the range of from preferably 600 to 640 nm r and a display employing these layers is preferred. At least these three layers may be laminated in order to prepare a white emission layer. A non-light emission layer may be provided as an intermediate layer between these emission layers. It is preferred that the organic EL device of the invention is a white emission layer or an illuminating device employing the same.

Each layer constituting the organic EL device of the invention will be explained below.

<<Light Emission Layer>>

The light emission layer in the invention is a layer where electrons and holes, injected from electrodes, an electron transporting layer or a hole transporting layer, are recombined to emit light. The portions where light emits may be in the light emission layer or at the interface between the light emission layer and the layer adjacent thereto.

The total thickness of the light emission layer is not particularly limited. In view of improving layer uniformity and stability of emitted light color against driving electric current without requiring unnecessary high voltage on light emission, the above thickness is adjusted to be in the range of preferably from 2 nm to 5 μm, more preferably from 2 to 200 nm, and still more preferably from 10 to 20 nm.

Employing an emission dopant or a host compound each described later, the light emission layer is formed according to a known thin layer formation method such as a vacuum deposition method, a spin coat method, a casting method, an LB method or an ink jet method.

The light emission layer of the organic EL device of the invention preferably contains a host compound and at least one of an emission dopant (also referred to as phosphorescence dopant or a phosphorescence emission dopant) and a fluorescent dopant.

(Host Compound (also referred to as Emission Host))

The host compound used in the invention will be explained below.

Herein, the host compound in the invention is defined as a compound which is contained in the light emission layer in an amount of not less than 20% by weight and which has a phosphorescence quantum yield at room temperature (25° C.) of less than 0.1. The phosphorescence quantum yield of the host compound is preferably less than 0.01. The content of the host compound in the light emission layer is preferably not less than 20% by weight.

Known host compounds may be used singly or as an admixture of plural kinds thereof. Usage of plural host compounds can adjust charge transfer, and obtain an organic EL device with high efficiency. Further, usage of plural emission dopants described later can mix light with a different color, and can emit light with any color.

The emission host used in the invention may be a conventional low molecular weight compound, a polymeric compound having a repeating unit or a low molecular weight compound (evaporation-polymerizable emission host) with a polymerizable group such as a vinyl group or an epoxy group.

The known host compound used in combination is preferably a compound with high Tg (glass transition temperature), which has a hole and electron transporting ability, and prevents the emission wavelength shifting to longer wavelength.

Typical examples of the host compound include those described in the following Documents.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

(Emission Dopant)

The emission dopant in the invention will be explained.

As the emission dopant in the invention, a fluorescent dopant (also referred to as a fluorescent compound) or a phosphorescence emission dopant (also referred to as a phosphorescence emitter, a phosphorescent compound, a phosphorescence emission compound or a phosphorescent dopant) can be used. As the emission dopant (also referred to simply as emission material) used in the light emission layer or the emission unit of the organic EL device of the invention, a phosphorescence emission dopant is preferably used in addition to the host compound as described above in obtaining an organic EL device with high emission efficiency.

(Phosphorescence Emission Dopant)

The phosphorescence emission dopant in the invention will be explained.

The phosphorescence emission dopant in the invention is a compound which emits light from the excited triplet, can emit phosphorescence at room temperature (25° C.), and has a phosphorescent quantum yield at 25° C. of not less than 0.01. The phosphorescent quantum yield at 25° C. is preferably not less than 0.1.

The phosphorescent quantum yield can be measured according to a method described in the fourth edition "Jikken Kagaku Koza 7", Bunko II, page 398 (1992) published by Maruzen. The phosphorescent quantum yield can be measured in a solution employing various kinds of solvents. The phosphorescence emission dopant in the invention is a compound, in which the phosphorescent quantum yield measured employing any one of the solvents satisfies the above-described definition (not less than 0.01).

The light emission of the phosphorescence emission dopant is divided in two types in principle, one is an energy transfer type in which recombination of a carrier occurs on the host to which the carrier is transported to excite the host, the resulting energy is transferred to the phosphorescence emission dopant, and light is emitted from the phosphorescence emission dopant, and the other is a carrier trap type in which recombination of a carrier occurs on the phosphorescence emission dopant, a carrier trap material, and light is emitted from the phosphorescence emission dopant. However, in each type, it is necessary that energy level of the phosphorescence emission dopant in excited state is lower than that of the host compound in excited state.

The phosphorescence emission dopant is suitably selected from those used in the light emission layer of an organic EL device.

The phosphorescence emission dopant in the invention is preferably a metal complex containing a metal belonging to a group VIII of the periodic table as a center metal, and is more preferably an iridium compound, an osmium compound, a platinum compound (a platinum complex) or a rare earth compound, and most preferably an iridium compound.
Examples of the phosphorescence emission dopant used in the invention will be listed below, but the invention is not limited thereto. These compounds can be synthesized according to a method described in Inorg. Chem. Vol. 40, 1704-1711.
1-1
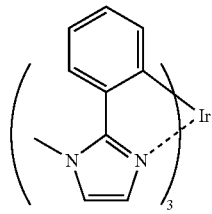
1-2
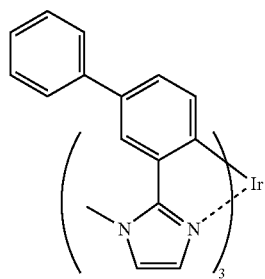
1-3
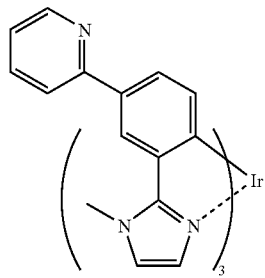
1-4
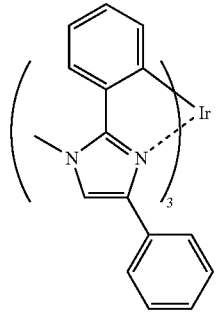
1-5
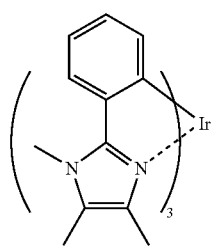
1-6
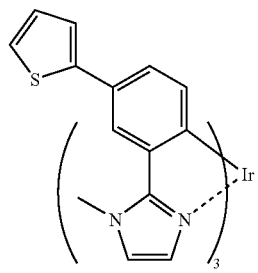
1-7
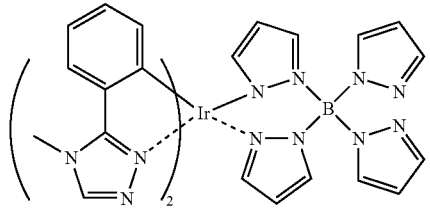
1-8
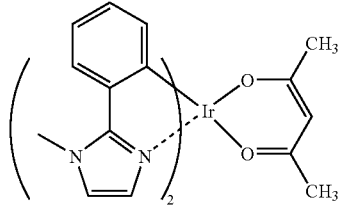
1-9
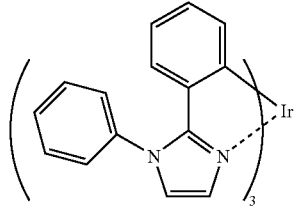
1-10
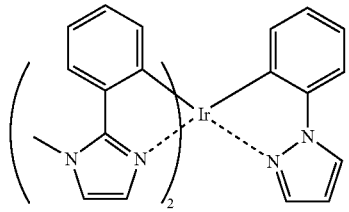
1-11
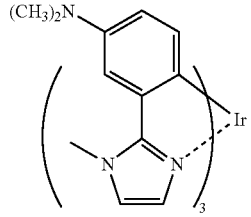
1-12
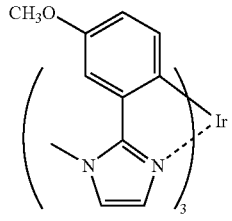

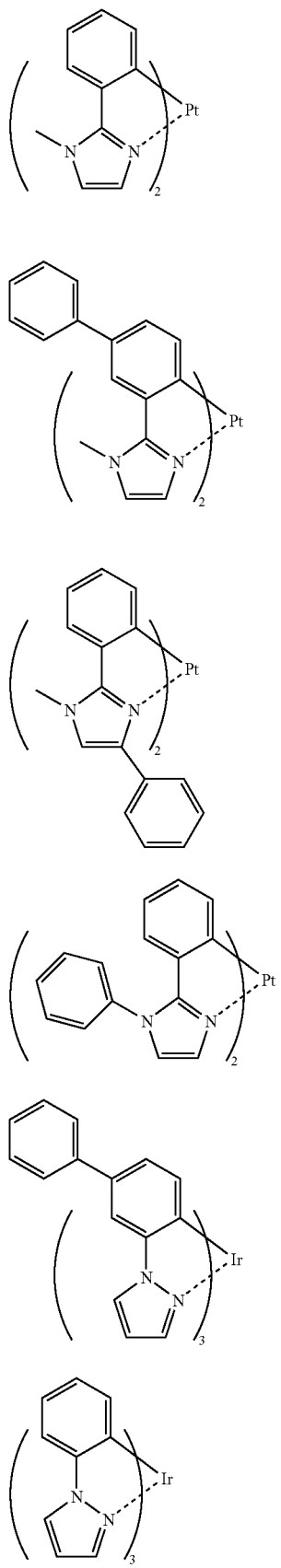
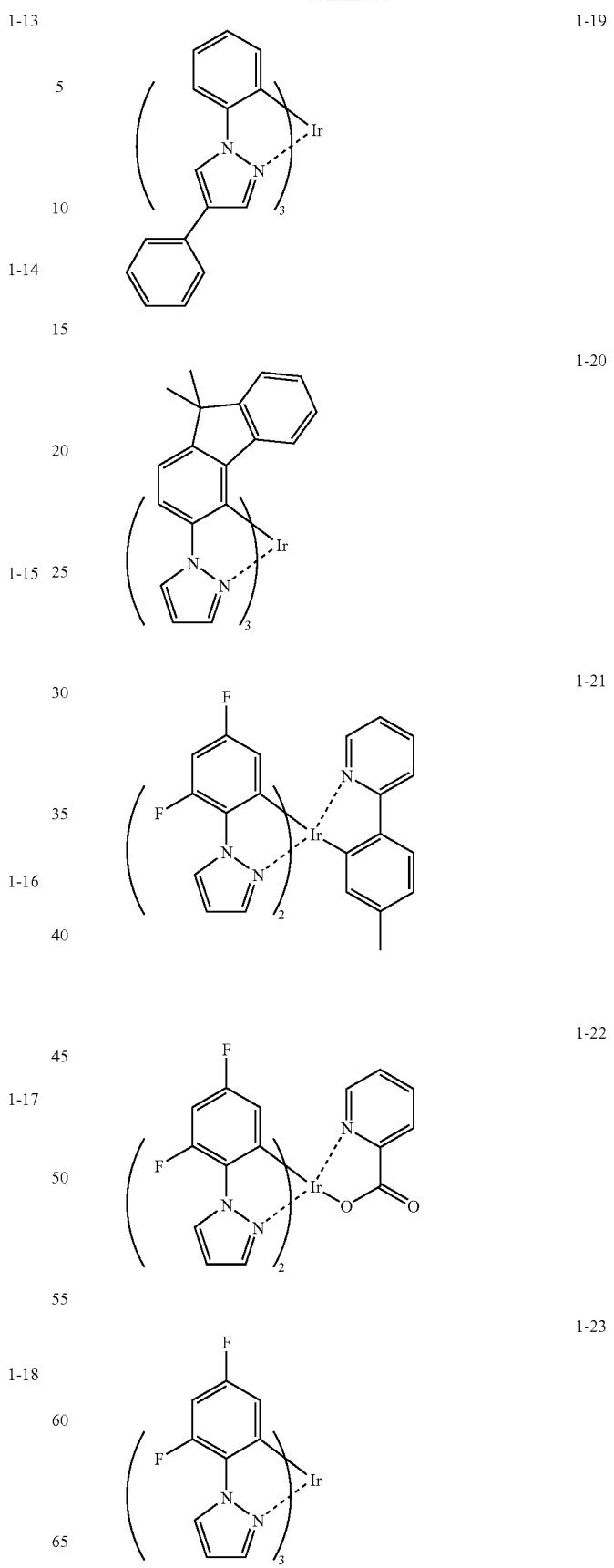

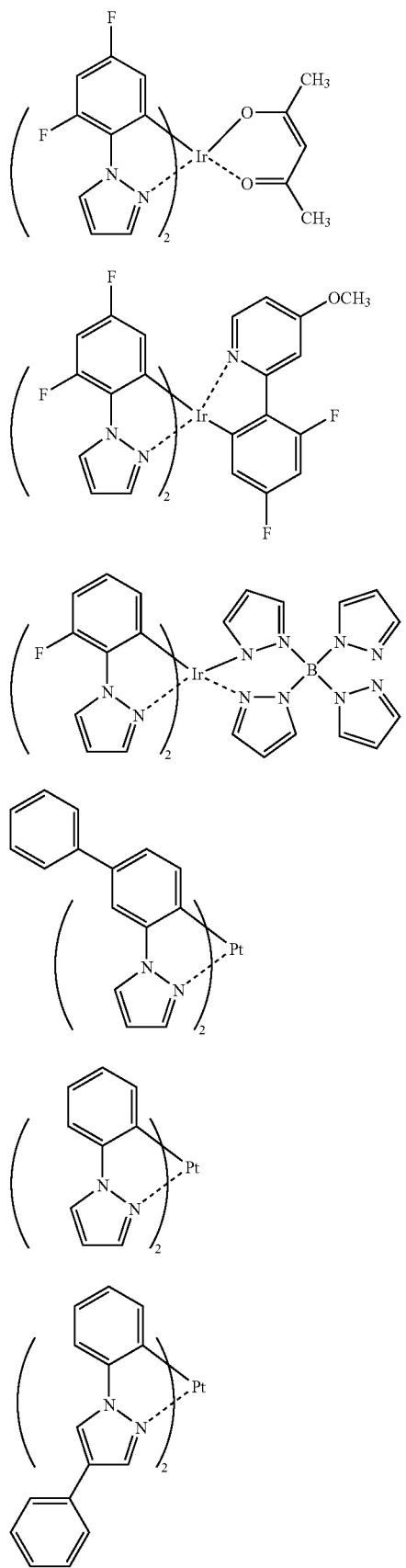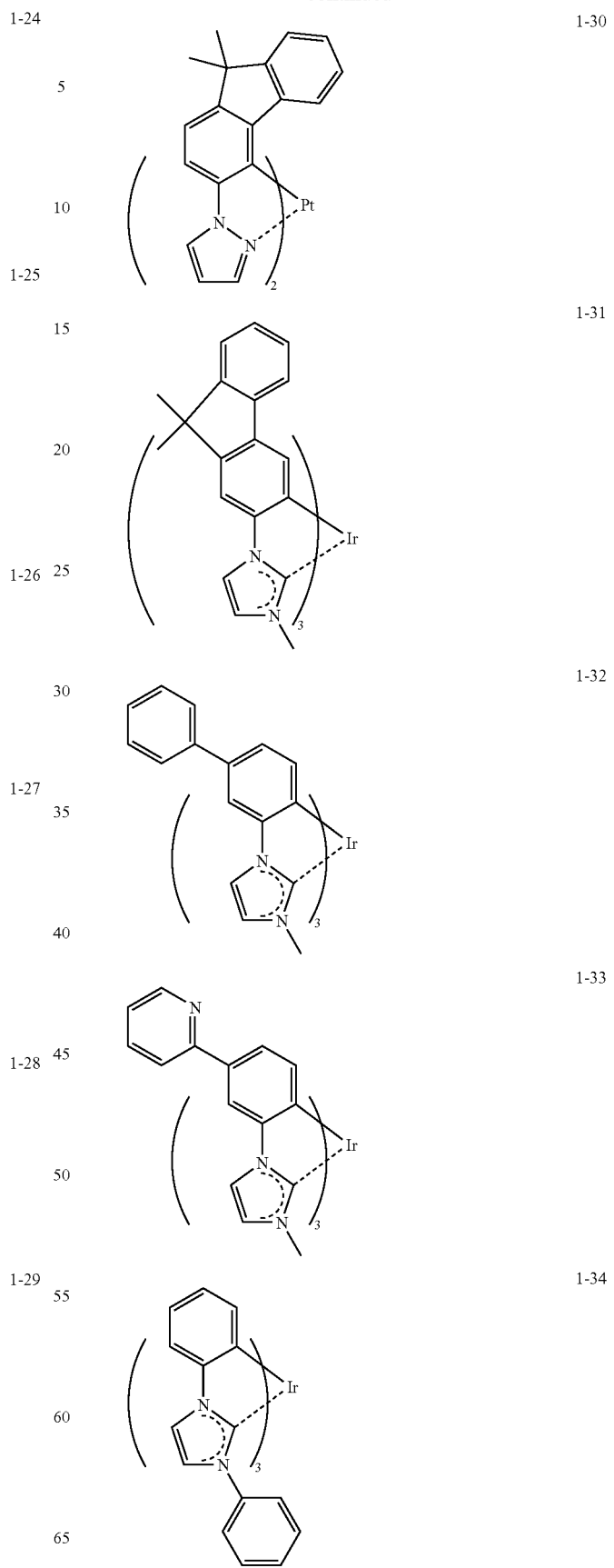

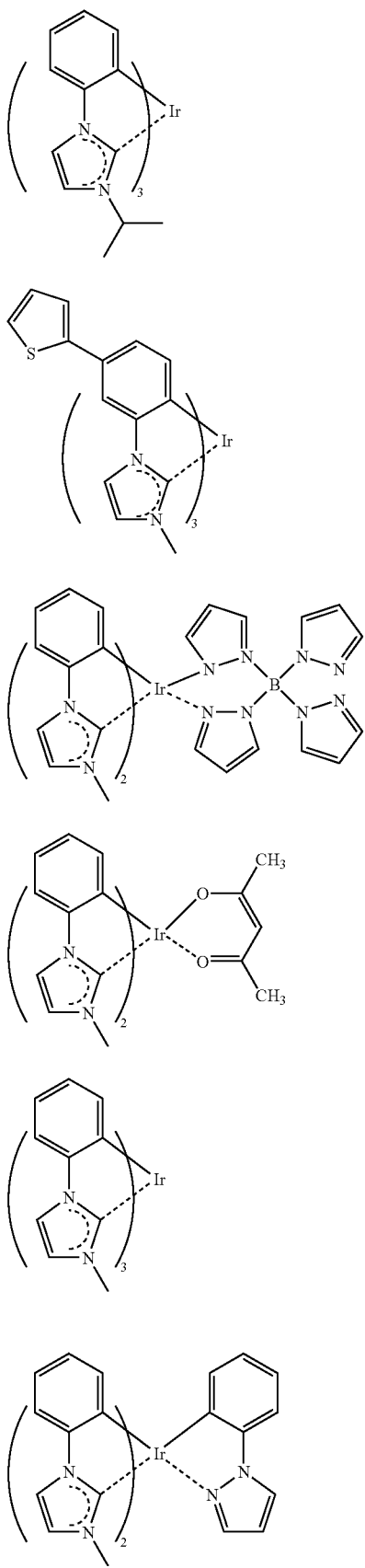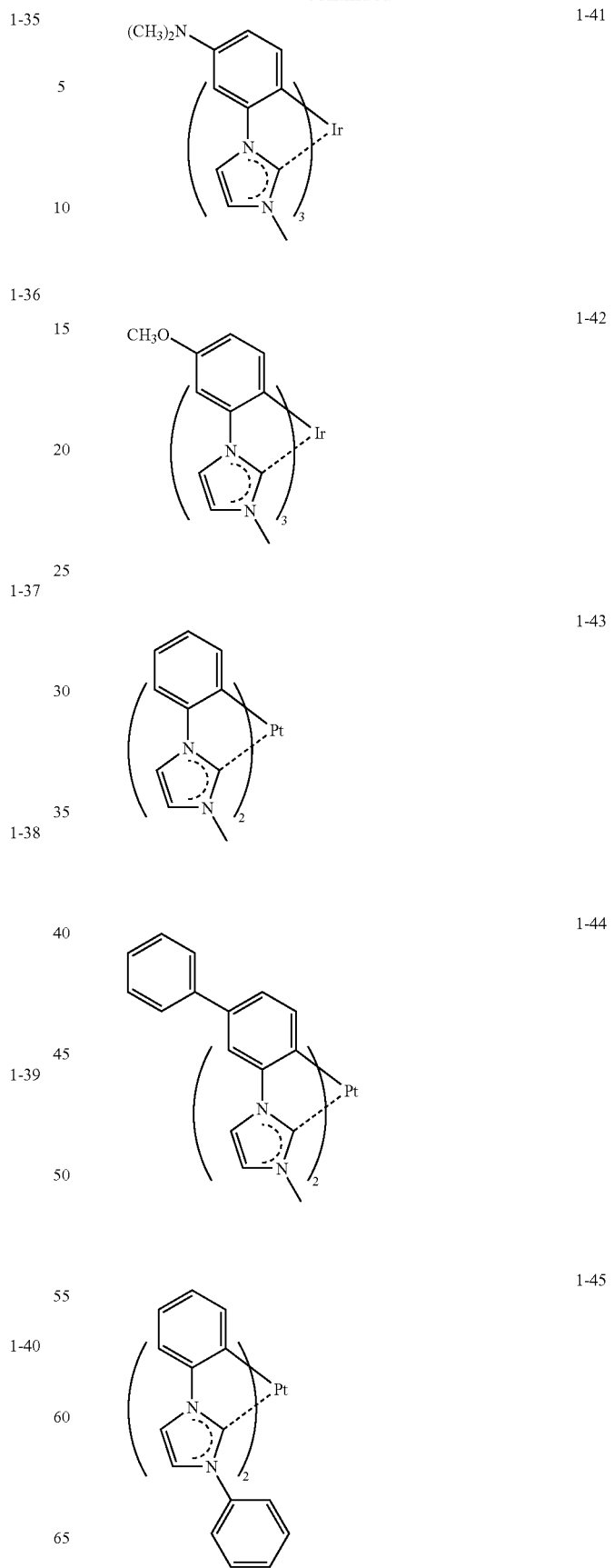

-continued
1-46
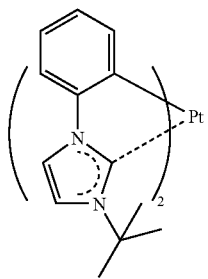
1-47
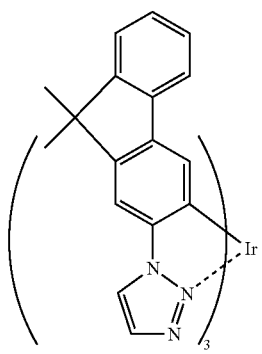
1-48
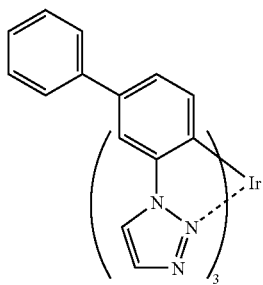
1-49
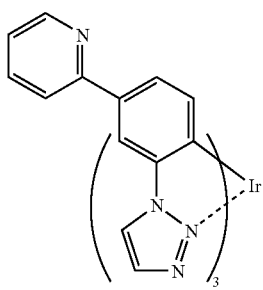
1-50
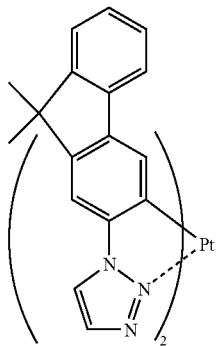
-continued
1-51
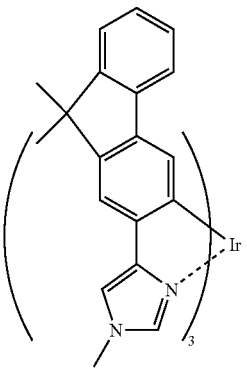
1-52
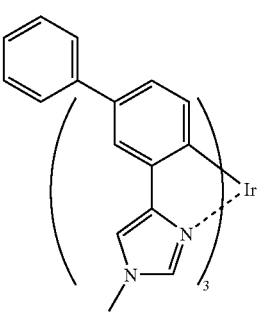
1-53
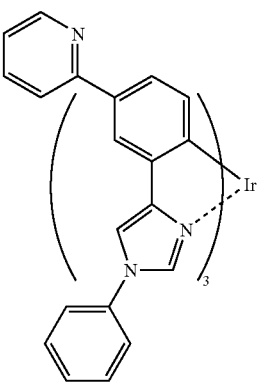
1-54

1-55
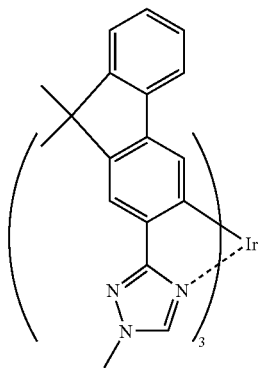
1-56
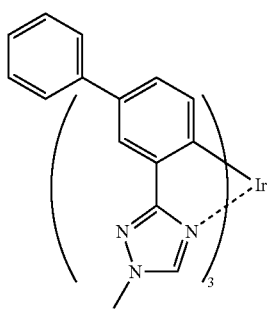
1-57
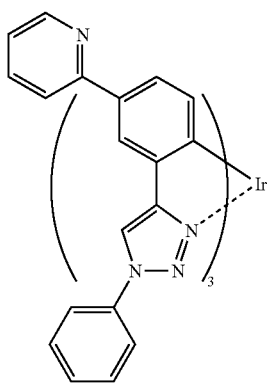
1-58
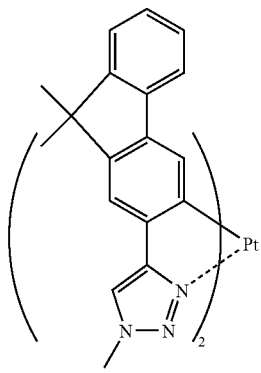
1-59
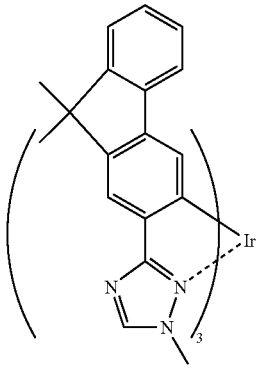
1-60
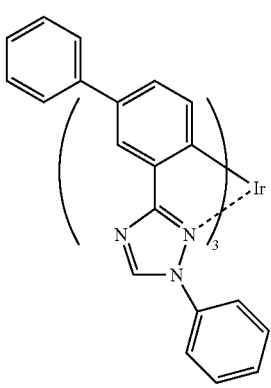
1-61
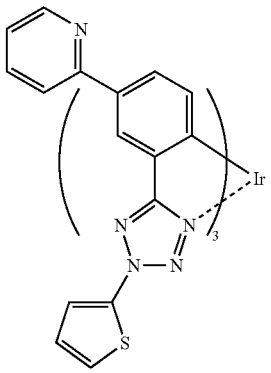
1-62
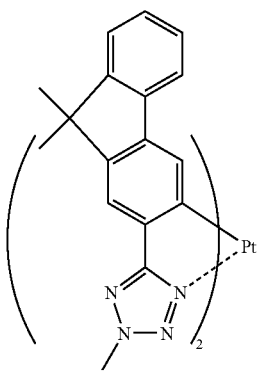

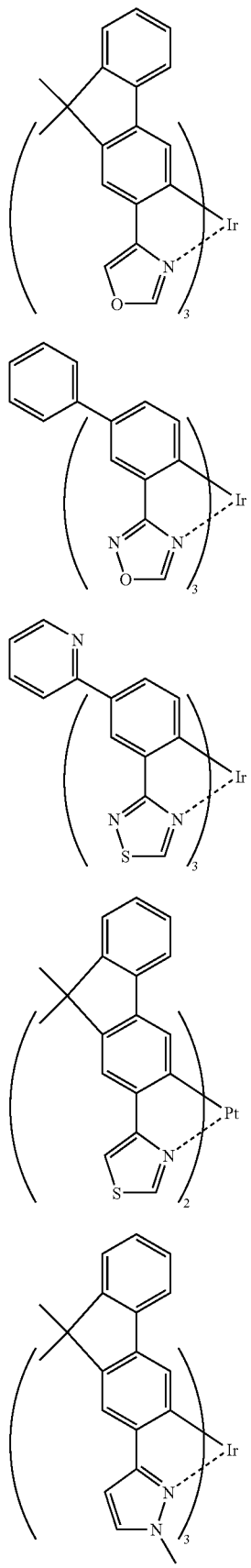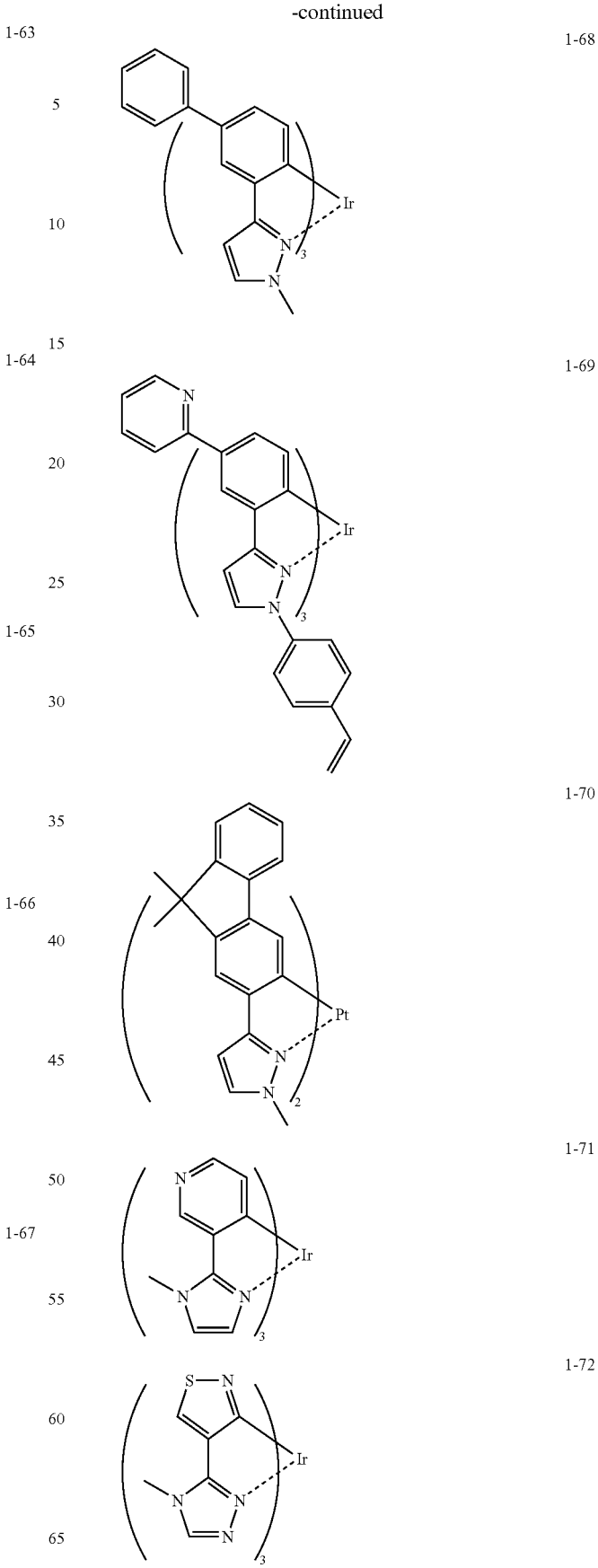

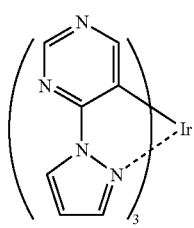
1-73
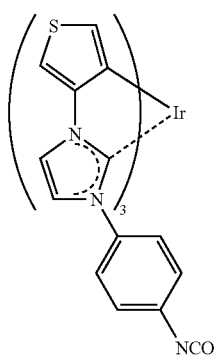
1-74
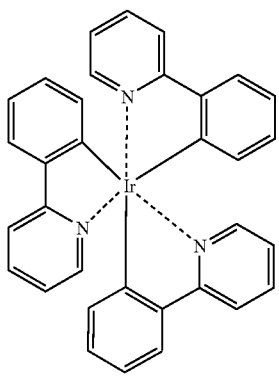
Ir-1
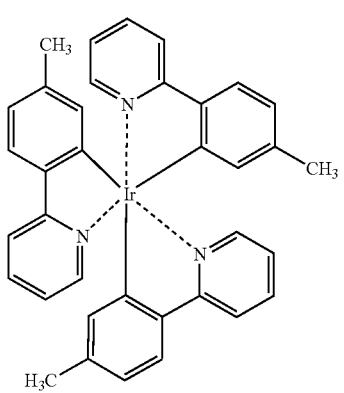
Ir-2
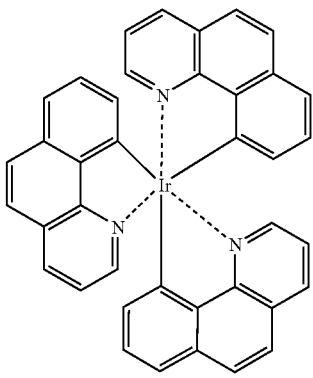
Ir-3
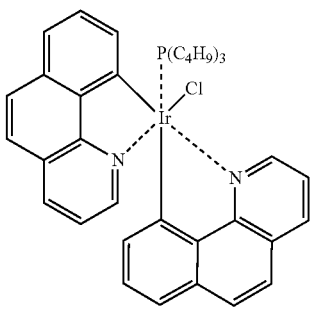
Ir-4
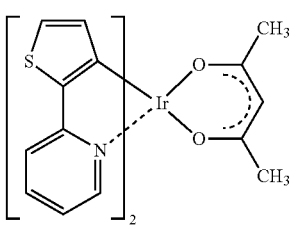
Ir-5
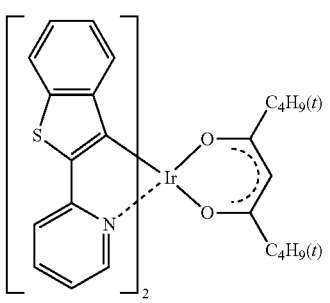
Ir-6
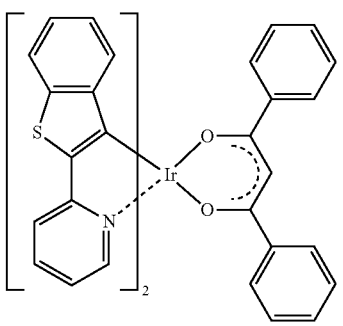
Ir-7

Ir-8
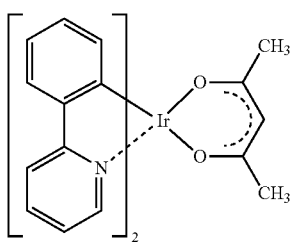
Ir-9
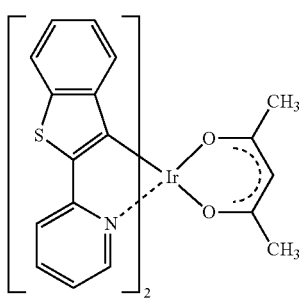
Ir-10
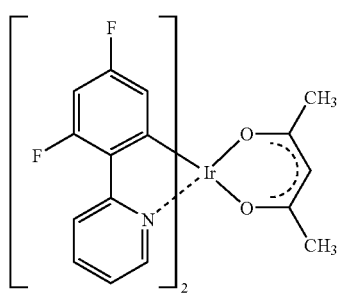
Ir-11
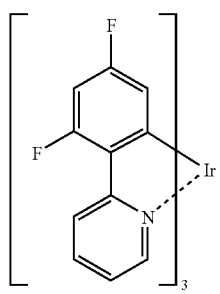
Ir-12
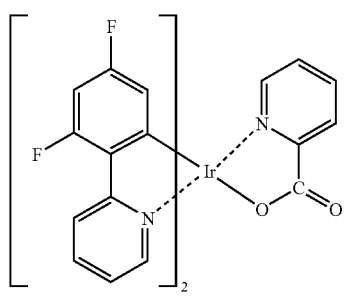
Ir-13
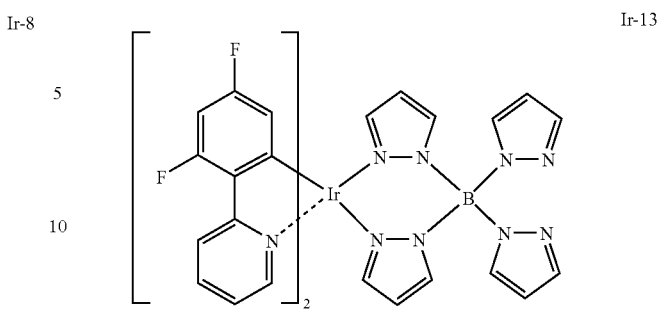
Ir-14
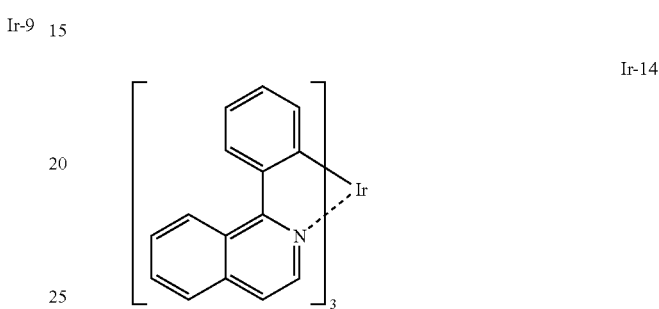
Pt-1
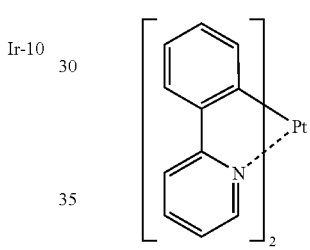
Pt-2
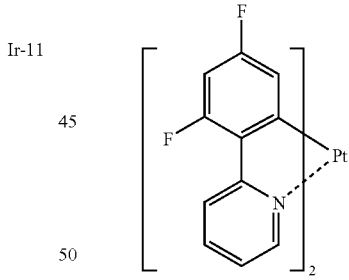
Pt-3
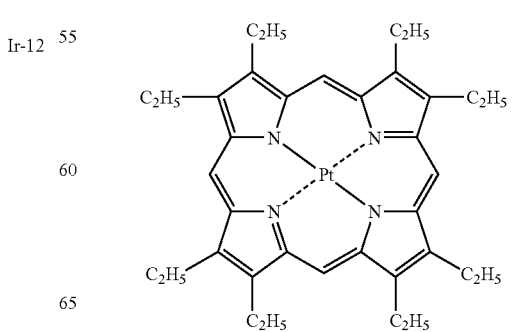

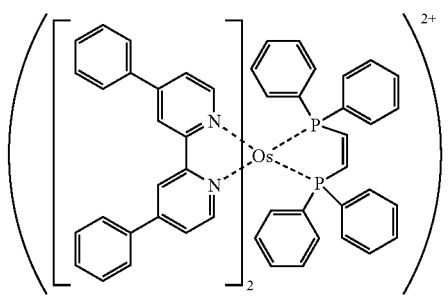

A-1

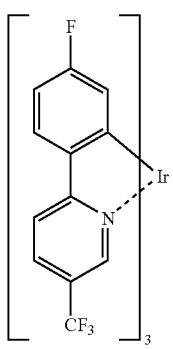

D-1

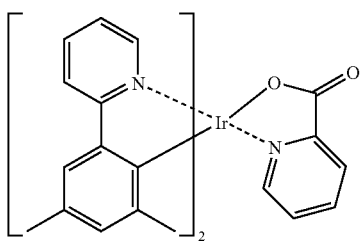

D-2

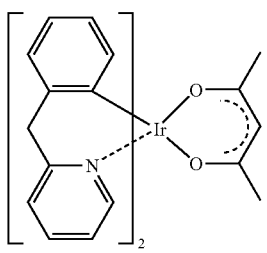

D-3

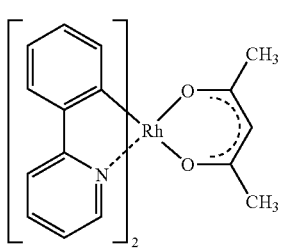

D-4

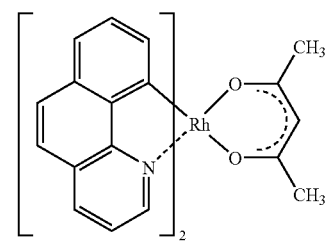

D-5

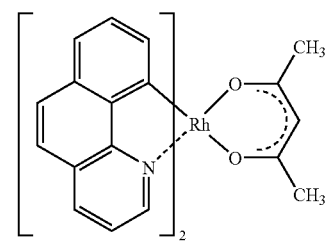

D-6

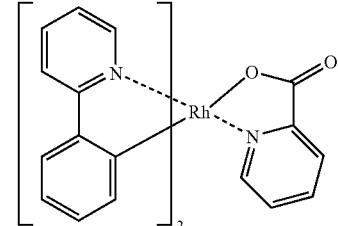

Rh-1

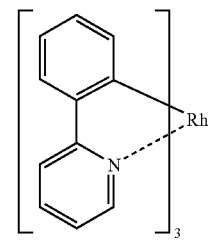

Rh-2

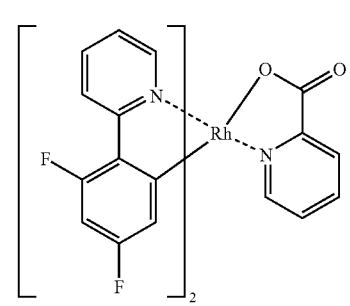

Rh-3

(Fluorescent Dopant (also referred to as Fluorescent Compound)) Examples of the fluorescent dopant (fluorescent compound) include a coumarin dye, a cyanine dyes a chloconium dye, a squarylium dye, an oxobenzanthracene dye, a fluorescene dye, a rhodamine dye, a pyrylium dye, a perylene dye, a stilbene dye, a polythiophene dye and rare earth complex type fluorescent compound.

Next, an injecting layer, a blocking layer, and an electron transporting layer used in the constituent layer of the organic EL device of the invention will be explained.

<<Injecting Layer: Electron Injecting Layer, Hole Injecting Layer>>

The injecting layer is optionally provided, for example, an electron injecting layer or a hole injecting layer, and may be provided between the anode and the light emission layer or hole transporting layer, and between the cathode and the light emission layer or electron transporting layer as described above.

The injecting layer herein referred to is a layer provided between the electrode and an organic layer in order to reduce the driving voltage or to improve of light emission efficiency. As the buffer layer there are a hole injecting layer (an anode buffer layer) and an electron injecting layer (a cathode buffer layer), which are described in "Electrode Material" page 123, Div. 2 Chapter 2 of "Organic EL device and its frontier of industrialization" (published by NTS Corporation, Nov. 30, 1998) in detail.

The anode buffer layer (hole injecting layer) is described in Japanese Patent O.P.I. Publication Nos. 9-45479, 9-260062, and 8-288069 etc., and its examples include a phthalocyanine buffer layer represented by a copper phthalocyanine layer, an oxide buffer layer represented by a vanadium oxide layer, an amorphous carbon buffer layer, a polymer buffer layer employing an electroconductive polymer such as polyaniline (emeraldine), and polythiophene, etc.

The cathode buffer layer (electron injecting layer) is described in Japanese Patent O.P.I. Publication Nos. 6-325871, 9-17574, and 10-74586, etc. in detail, and its examples include a metal buffer layer represented by a strontium or aluminum layer, an alkali metal compound buffer layer represented by a lithium fluoride layer, an alkali earth metal compound buffer layer represented by a magnesium fluoride layer, and an oxide buffer layer represented by an aluminum oxide. The buffer layer (injecting layer) is preferably very thin and has a thickness of preferably from 0.1 nm to 5 μm depending on kinds of the material used.

<<Inhibiting Layer: Hole Inhibiting Layer, Electron Inhibiting Layer>>

The inhibiting layer is a layer provided if necessary in addition to the fundamental constituent layer as described above, and is for example a hole inhibiting layer as described in Japanese Patent O.P.I. Publication Nos. 11-204258, and 11-204359, and on page 237 of "Organic EL device and its frontier of industrialization" (published by NTS Corporation, Nov. 30, 1998).

The hole inhibiting layer is an electron transporting-layer in a broad sense, and is comprised of material having an ability of transporting electrons but an extremely poor ability of holes, which can increase a recombination probability of electrons and holes by transporting electrons and blocking holes. Further, the constitution of an electron transporting layer described later can be used in the hole inhibiting layer in the invention as necessary.

The hole inhibiting layer in the organic EL device of the invention is preferably provided to be in contact with a light emission layer.

It is preferred that the hole inhibiting layer contains an azacarbazole derivative which is denoted as the host compound described above.

Further, in the invention, when there are a plurality of light emission layers which emit a plurality of different color lights, it is preferable that a light emission layer which emits a light having emission maximum in the shortest wavelength of all the light emission layers is provided closest to the anode. In such a case, it is preferred that a hole inhibiting layer is additionally provided between the above light emission layer which emits a light having emission maximum in the shortest wavelength and a light emission layer which is provided closest to the anode, except for the above layer. Further, it is preferred that at least 50% by weight of compounds, which are incorporated in the hole inhibiting layer arranged in the above position, has an ionization potential 0.3 eV higher than that of the host compound contained in the light emission layer which emits a light having emission maximum in the shortest wavelength.

Ionization potential is defined as energy required to transfer an electron in the highest occupied molecular orbital to the vacuum level, and can be determined by the methods described below:

(1) The ionization potential can be obtained as a value obtained by rounding to one decimal a value (in terms of eV), which is calculated by performing structural optimization employing Gaussian 98 (Gaussian 98, Revision A. 11.4 M J. Frisch, et al., Gaussian, Inc., Pittsburgh Pa., 2002), which is a software for molecular orbital calculation of Gaussian, Inc., and B3LYP/6-31G* as a key word, and the calculated value (being the value in terms of eV unit) is rounded off at the second decimal place. Background in which the calculated value above is effective is that the calculated value obtained by the above method and experimental values exhibit high correlation.

(2) It is also possible to obtain ionization potential via a direct measurement method employing a photoelectron spectroscopy. For example, it is possible to appropriately employ a low energy electron spectrometer "Model AC-1", produced by Riken Keiki Co., Ltd., or a method known as ultraviolet photoelectron spectroscopy.

On the other hand, the electron blocking layer is an hole transporting layer in a broad sense, and is comprised of material having an ability of transporting holes but an extremely poor ability of electrons, which can increase a recombination probability of electrons and holes by transporting holes and blocking electrons. The thickness of the hole inhibiting layer or electron transporting layer is preferably from 3 to 100 nm, and more preferably from 5 to 30 nm.

<<Hole Transporting Layer>>

The hole transporting layer is comprised of a hole transporting material having an ability of transporting holes, and a hole injecting layer and an electron blocking layer are included in the hole transporting layer in a broad sense. The hole transporting layer may be a single layer or plural layers.

The hole transporting material has a hole injecting ability, a hole transporting ability or an ability to form a barrier to electrons, and may be either an organic substance or an inorganic substance. Examples of thereof include a triazole derivative, an oxadiazole derivative, an imidazole derivative, a polyarylalkane derivative, a pyrazoline derivative and a pyrazolone derivative, a phenylenediamine derivative, an arylamine derivative, an amino substituted chalcone derivative, an oxazole derivative, a styryl anthracene derivative, a fluorenone derivative, a hydrazone derivative, a stilbene derivative, a silazane derivative, an aniline copolymer, and an electroconductive oligomer, particularly a thiophene oligomer.

As the hole transporting material, those described above are used, but a porphyrin compound, an aromatic tertiary amine compound, or a styrylamine compound is preferably used, and an aromatic tertiary amine compound is more preferably used.

Typical examples of the aromatic tertiary amine compound and styrylamine compound include N,N,N',N'-tetraphenyl-4,4'-diaminophenyl, N,N'-diphenyl-N,N'-bis(3-methylphenyl)-[1,1'-biphenyl]-4,4'-diamine (TPD), 2,2'-bis(4-di-p-tolylaminophenyl)propane, 1,1'-bis(4-di-p-tolylaminophenyl)cyclohexane, N,N,N',N'-tetra-p-tolyl-4,4'-diaminobiphenyl, 1,1'-bis(4-di-p-tolylaminophenyl)-4-phenylcyclohexane, bis(4-dimethylamino-2-methylphenyl)phenylmethane, bis(4-di-p-tolylaminophenyl)-phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quardriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostylbenzene, N-phenylcarbazole, compounds described in U.S. Pat. No. 5,061,569 which have two condensed aromatic rings in the molecule thereof such as 4,4'-bis[N-(1-naphthyl)-N-phenylamino]biphenyl (NPD), and compounds described in Japanese Patent O.P.I. Publication No. 4-308688 such as 4,4',4"-tris[N-(3-methylphenyl)-N-phenylamino]-triphenylamine (MTDATA) in which three triphenylamine units are bonded in a starburst form.

A polymer in which the material mentioned above is introduced in the polymer chain or a polymer having the material as the polymer main chain can be also used. As the hole injecting material or the hole transporting material, inorganic compounds such as p-type-Si and p-type-SiC are usable.

So-called p-type hole transporting materials as disclosed in JP-A No. 11-251067 or described in the literature of J. Huang et al. (Applied Physics Letters 80 (2002), p. 139) are also applicable. In the present invention, these materials are preferably utilized since an emitting device exhibiting a higher efficiency is obtained.

The hole transporting layer can be formed by layering the hole transporting material by a known method such as a vacuum deposition method, a spin coat method, a casting method, an ink jet method, and an LB method. The thickness of the hole transporting layer is not specifically limited, but is ordinarily from 5 nm to 5 μm, and preferably from 5 to 200 nm. The hole transporting layer may be composed of a single layer structure comprising one or two or more of the materials mentioned above.

A positive hole transporting layer having high p-type property doped with impurity can be utilized. Example thereof includes those described in JP-A-H04-297076, JP-A-2000-196140, JP-A-2001-102175, and J. Appl. Phys., 95, 5773 (2004) and so on.

It is preferable in the invention to employ such a positive hole transporting layer having high p-type property, since a device with lower power consumption can be prepared.

<<Electron Transporting Layer>>

The electron transporting layer comprises a material (an electron transporting material) having an electron transporting ability, and in a broad sense refers to an electron injecting layer or a hole blocking layer. The electron transporting layer can be provided as a single layer or plural layers.

An electron transporting material (which serves also as a hole inhibiting material) used in a single electron transporting layer or in the electron transporting layer closest to the cathode in plural electron transporting layers has a function of incorporating electrons injected from a cathode to a light emission layer, and is selected from known compounds. Examples thereof include a nitro-substituted fluorene, derivative, a diphenylquinone derivative, a thiopyran dioxide derivative, a carbodiimide, a fluolenylidenemethane derivative, an anthraquinodimethane, an anthrone derivative, and an oxadiazole derivative. Moreover, a thiadiazole derivative which is formed by substituting the oxygen atom in the oxadiazole ring of the foregoing oxadiazole derivative with a sulfur atom, and a quinoxaline derivative having a quinoxaline ring known as an electron withdrawing group are usable as the electron transporting material. A polymer in which the material mentioned above is introduced in the polymer side chain or a polymer having the material as the polymer main chain can be also used.

A metal complex of an 8-quinolynol derivative such as aluminum tris-(8-quinolynol) (Alq$_3$), aluminum tris-(5,7-dichloro-8-quinolynol), aluminum tris-(5,7-dibromo-8-quinolynol) r aluminum tris-(2-methyl-8-quinolynol), aluminum tris-(5-methyl-8-quinolynol), or zinc bis-(8-quinolynol) (Znq$_2$), and a metal complex formed by replacing the central metal of the foregoing complexes with another metal atom such as In, Mg, Cu, Ca, Sn, Ga or Pb, can be used as the electron transporting material. Furthermore, a metal free or metal-containing phthalocyanine, and a derivative thereof, in which the molecular terminal is replaced by a substituent such as an alkyl group or a sulfonic acid group, are also preferably used as the electron transporting material. The distyrylpyrazine derivative exemplified as a material for the light emission layer may preferably be employed as the electron transporting material. An inorganic semiconductor such as n-type-Si and n-type-SiC may also be used as the electron transporting material in a similar way as in the hole transporting layer.

The electron transporting layer can be formed employing the above-described electron transporting materials and a known method such as a vacuum deposition method, a spin coat method, a casting method, a printing method including an ink jet method or an LB method. The thickness of electron transporting layer is not specifically limited, but is ordinarily from 5 nm to 5 μm, and preferably from 5 to 200 nm. The electron transporting layer may be composed of a single layer comprising one or two or more of the electron transporting material.

An electron transporting layer having high n-type property doped with impurity can be utilized. Example thereof includes those described in JP-A-H04-297076, JP-A-H10-270172, JP-A-2000-196140, JP-A-2001-102175, and J. Appl. Phys., 95, 5773 (2004) and so on.

It is preferable in the invention to employ such an electron transport layer having high n-type property, since an element with lower power consumption can be prepared.

<<Anode>>

For the anode of the organic EL device, a metal, an alloy, or an electroconductive compound each having a high working function (not less than 4 eV), and mixture thereof are preferably used as the electrode material. Concrete examples of such an electrode material include a metal such as Au, and a transparent electroconductive material such as CuI, indium tin oxide (ITO), SnO$_2$, or ZnO.

A material such as IDIXO (In$_2$O$_3$—ZnO) capable of forming an amorphous and transparent conductive layer may be used. The anode may be prepared by forming a thin layer of the electrode material according to a depositing or spattering method, and by forming the layer into a desired pattern according to a photolithographic method. When required precision of the pattern is not so high (not less than 100 μm), the pattern may be formed by depositing or spattering of the electrode material through a mask having a desired form.

When a coatable material such as an organic conductive compound is used, a wet coating method such as a printing method or a coating method can be used. When light is emitted through the anode, the transmittance of the anode is preferably 10% or more, and the sheet resistance of the anode is preferably not more than several hundred Ω/□. The thickness of the layer is ordinarily within the range of from 10 nm to 1 μm, and preferably from 10 to 200 nm, although it may vary due to kinds of materials used.

<<Cathode>>

On the other hand, for the cathode, a metal (also referred to as an electron-injecting metal), an alloy, and an electroconductive compound each having a low working function (not more than 4 eV), and a mixture thereof is used as the electrode material. Concrete examples of such an electrode material include sodium, sodium-potassium alloy, magnesium, lithium, a magnesium/copper mixture, a magnesium/silver mixture, a magnesium/aluminum mixture, magnesium/indium mixture, an aluminum/aluminum oxide ($Al_2O_3$) mixture, indium, a lithium/aluminum mixture, and a rare-earth metal. Among them, a mixture of an electron injecting metal and a metal higher in the working function than that of the electron injecting metal, such as the magnesium/silver mixture, magnesium/aluminum mixture, magnesium/indium mixture, aluminum/aluminum oxide ($Al_2O_3$) mixture, lithium/aluminum mixture, or aluminum is suitable from the view point of the electron injecting ability and resistance to oxidation. The cathode can be prepared forming a thin layer of such an electrode material by a method such as a deposition or spattering method.

The sheet resistance as the cathode is preferably not more than several hundred $\Omega/\square$, and the thickness of the layer is ordinarily from 10 nm to 5 μm, and preferably from 50 to 200 nm. It is preferable in increasing the light emission efficiency that either the anode or the cathode of the organic EL device is transparent or semi-transparent.

After a layer of the metal described above as a cathode is formed to give a thickness of from 1 to 20 nm, a layer of the transparent electroconductive material as described in the anode is formed on the resulting metal layer, whereby a transparent or semitransparent cathode car be prepared. Employing the cathode, a device can be manufactured in which both anode and cathode are transparent.

<<Substrate>>

The substrate (also referred to as a base body, a base plate, a base material or a support) employed for the organic EL device of the invention is not restricted to specific kinds of materials such as glass and plastic, as far as it is transparent. When light is taken out from the substrate side, the substituent is preferably transparent.

Examples of the substrate preferably used include glass, quartz and light transmissible plastic film. Especially preferred one is a resin film capable of providing flexibility to the organic EL device.

Examples of materials for the resin film include polyesters such as polyethylene terephthalate (PET) and polyethylene naphthalate (PEN), polyethylene, polypropylene, cellophane, cellulose esters and their derivatives such as cellulose diacetate, cellulose triacetate, cellulose acetate butylate, cellulose acetate propionate (CAP), cellulose acetate phthalate (TAC), and cellulose nitrate, polyvinylidene chloride, polyvinylalcohol, polyethylenevinylalcohol, syndiotactic polystyrene, polycarbonate, norbornane resin, polymethylpentene, polyetherketone, polyimide, polyether sulfone (PES), polyphenylene sulfide, polysulfones, polyether imide, polyetherketone imide, polyamide, fluorine resin, nylon, polymethyl methacrylate, acryl or polyarylates, and cyclo-olefin resins such as ARTON (commercial name, manufactured by JSR Corp.) or APEL (commercial name, manufactured by Mitsui Chemicals Inc.).

On the surface of the resin film, an inorganic or organic cover film or a hybrid cover film comprising the both may be formed, and the cover film is preferably one with a barrier ability having a vapor permeability (at 25±0.5° C. and at (90±2)% RH) of not more than 0.01 g/(m²·24h) measured by a method stipulated by JIS K 7129-1992, and more preferably one with a high barrier ability having an oxygen permeability of not more than $10^{-3}$ ml/(m²·24 hr·MPa) as well as a vapor permeability of not more than $10^{-5}$ g/(m²·24 h), measured by a method stipulated by JIS K 7126-1987.

Any materials capable of preventing penetration of substance such as moisture and oxygen causing degradation of the device are usable for forming the barrier film, and for example, silicon oxide, silicon dioxide and silicon nitride are usable. It is more preferred that the barrier film has a multi-laminated layer structure composed of a layer of the inorganic material and a layer of an organic material for improving fragility of the film. It is preferable that the both layers are alternatively laminated for several times though there is no limitation as to the laminating order of the inorganic layer and the organic layer.

The method for forming the barrier film is not specifically limited and, for example, a vacuum deposition method, a spattering method, a reaction spattering method, a molecule beam epitaxy method, a cluster-ion beam method, an ion plating method, a plasma polymerization method, an atmospheric pressure plasma polymerization method, a plasma CVD method, a laser CVD method, a heat CVD method and a coating method are applicable, and the atmospheric pressure plasma polymerization method as described in JP A 2004-68143 is particularly preferable.

As the opaque substrate, for example, a plate of metal such as aluminum and stainless steel, a film or plate of opaque resin and a ceramic substrate are cited.

The external light emission efficiency of the organic electroluminescent device of the invention is preferably not less than 1%, and more preferably not less than 5% at room temperature. Herein, external quantum yield (%) is represented by the following formula:

External quantum yield (%)=(the number of photons emitted to the exterior of the organic electroluminescent device×100)/(the number of electrons supplied to the organic electroluminescent device)

A hue improving filter such as a color filter may be used in combination or a color conversion filter which can convert from emission light color from an organic EL device to multi-color employing a fluorescent compound may be used in combination. In the case where the color conversion filter, the λmax of the light emitted from the organic EL device is preferably not more than 480 nm.

<<Sealing>>

As the sealing means used in the invention, a method for pasting together with a sealing material, the electrodes and the substrate by an adhesive agent is applicable.

The sealing material is placed so as to cover the displaying area of the organic EL device and may have a flat plate shape or a concave plate shape, and the transparence and the electric insulation property thereof are not specifically limited.

Concretely, a glass plate, a polymer plate, a polymer film, a metal plate and a metal film can be cited. As the glass plate, a plate of soda-lime glass, barium strontium-containing glass, lead glass, alumino silicate glass, boron silicate glass or quartz is usable. As the polymer plate, a plate of polycarbonate, acryl resin, polyethylene terephthalate, polyether sulfide or polysulfone is usable.

As the metal plate, a plate composed of one or more kinds of metal selected from stainless steel, iron, copper, aluminum, magnesium, nickel, zinc, chromium, titanium, molybdenum, silicon, germanium and tantalum and an alloy of them is cited.

In the invention, the polymer film and the metal film are preferably used since the device can be made thinner. The polymer film is one having an oxygen permeability-of not more than $10^{-3}$ ml/(m²·24 hr·MPa), measured by a method stipulated by JIS K 7126-1987 and a vapor permeability (at 25±0.5° C. and at (90±2)% RH) of not more than $10^{-5}$ g/(m²·24h), measured by a method stipulated by JIS K 7129-1992.

For making the sealing material into the concave shape, a sandblast treatment and a chemical etching treatment are applicable. As the adhesive agent, a photo-curable and thermo-curable adhesive agent containing a reactive vinyl group of acryl type oligomer and a methacryl type oligomer, and a moisture curable adhesive agent such as 2-cyanoacrylate can be cited.

Epoxy type thermally and chemically (two liquid type) curable adhesive agents are applicable. Hot-melt type polyamide, polyester and polyolefin adhesive agents are applicable. A cationic curable type UV curable epoxy adhesive agent is also usable.

The organic EL device is degraded by heat in some cases, therefore, the adhesive agent capable of being cured to adhere within the temperature range of from room temperature to 80° C. is preferred. A moisture absorbing agent may be dispersed in the adhesive agent. Coating of the adhesive agent onto the adhering portion may be performed by a dispenser available on the market or printing by a screen printing.

It is preferred that a layer comprising an inorganic or organic material is provided on outside of the electrode placed on the side of facing to the substrate through an organic layer so as to cover the electrode and the organic layer and contact with the substrate to form a sealing layer. In such the case, a material for forming the sealing layer may be a material having a function to inhibit permeation of a substance such as water and oxygen causing degradation of the device, and for example, silicon oxide, silicon dioxide and silicon nitride are usable. The sealing layer preferably has a multi-laminated layer structure composed of a layer of the inorganic material and a layer of an organic material for improving fragility of the layer.

The method for forming the layer is not specifically limited and, for example, a vacuum deposition method, a spattering method, a reaction spattering method, a molecule beam epitaxy method, a cluster-ion beam method, an ion plating method, a plasma polymerization method, an atmospheric pressure plasma polymerization method, a plasma CVD method, a laser CVD method, a heat CVD method and a coating method are applicable.

In the space between the sealing material and the displaying portion of the organic EL Device, an inactive gas such as nitrogen or argon or an inactive liquid such as fluorinated hydrocarbon or silicone oil is preferably injected in the form of gas or liquid phase. The space can be made vacuum. A hygroscopic compound can be enclosed inside.

Examples of the hygroscopic compound include a metal oxide such as sodium oxide, potassium oxide, calcium oxide, barium oxide, magnesium oxide or aluminum oxide; a sulfate such as sodium sulfate, calcium sulfate, magnesium sulfate or cobalt sulfate; a metal halide such as calcium chloride, magnesium chloride, cesium fluoride, tantalum fluoride, cerium bromide, magnesium bromide, barium iodide or magnesium iodide; and a perchlorate such as barium perchlorate or magnesium perchlorate. An anhydride of the sulfate, halide and perchlorate is suitably applicable.

<<Protection Layer and Protection Plate>>

A protection layer or a protection plate may be provided on outside of the sealing layer of the side facing to the substrate through the organic layer or the outside of the sealing film for raising the mechanical strength of the device. Such a protection layer or plate is preferably provided since strength of the device is not so high even when sealing is carried out by the foregoing sealing layer. As materials for the protection layer or plate, the same glass plate, polymer plate or film or metal plate or film as those to be used for sealing are usable. The polymer film is preferably used from the viewpoint of light weight and thin layer formation property.

<<Light Takeout>>

It is generally said that, in the organic EL element, light is emitted in a layer whose refractive index (the refractive index is about 1.7 to 2.1) is higher than that of air, and only 15 to 20% of the light emitted in the light emission layer can be taken out. This is because the light which enters into the interface (interface of a transparent substrate and air) with the angle θ larger than a critical angle cannot be taken out of the device due to the total internal reflection, or because the light is totally reflected between the transparent substrate and the transparent electrode or between the transparent substrate and the light emission layer, so that the light gets away from the side of the device through the transparent electrode or the light emission layer.

Examples of a method to improve efficiency of the light takeout include a method to form concavity and convexity on the surface of the transparent substrate to prevent total internal reflection at the interface between the transparent substrate and air (for example, U.S. Pat. No. 4,774,435); a method to provide a light converging function to the substrate (for example, JP-A 863-314795); a method to provide a reflecting surface on the side of the element (for example, JP-A No. H01-220394); a method to provide a flat layer between the substrate and the light emission layer, the flat layer having an intermediate refractive index to form an anti-reflection layer (for example, refer to JP-A S62-172691); a method to provide a flat layer having a low refractive index between the substrate and the light emission layer (for example, JP-A 2001-202827); and a method to provide a diffraction grating between any of the substrate, transparent electrode and light emission layer (including the interlayer between the substrate and out side air) (for example JP-A H11-283751).

In the present invention, these methods can be used in combination with the organic electroluminescence device of the present invention. Also, a method of forming a flat layer having a lower refractive index than that of the substrate between the substrate and the light emission layer, or a method of forming a diffraction grating between any of the substrate, transparent electrode and light emission layer (including the interlayer between the substrate and out side air) can be preferably used.

In the present invention, an element exhibiting further higher luminance and durability can be obtained by combining these methods.

When a low refractive index medium having a thickness greater than the wavelength of the light is formed between the transparent electrode and the transparent substrate, the takeout efficiency of light which comes out of the transparent electrode increases with decreasing the refractive index of the medium.

As a low refractive index layer, aerogel, porous silica, magnesium fluoride and fluorine-containing polymer are cited, for example. Since the refractive index of the transparent substrate is generally 1.5 to 1.7, the refractive index of the low refractive index layer is preferably 1.5 or less and more preferably 135 or less.

The thickness of a low refractive index medium is preferably twice or more of the wavelength of the light in the medium, because when the thickness of the low refractive index medium is such that the electromagnetic wave exuded as an evanescent wave enters into the transparent substrate, the effect of the low refractive index layer is reduced.

A method to provide a diffraction grating at the interface where the total internal reflection occurs or in some of the medium has feature that the effect of enhancing the light takeout efficiency is high. The intension of this method is to take out the light which cannot come out due to such as total internal reflection between the layers among the light emitted in the light emission layer, by providing a diffraction grating between any of the layers or in any of the mediums (in the transparent substrate or in the transparent electrode), using the property of the diffraction grating that it can change the direction of light to a specific direction different from the direction of reflection due to so-called Bragg diffraction such as primary diffraction or secondary diffraction.

It is preferred that the diffraction grating to be provided has a two-dimensional periodic refractive index. This is because, since the light is emitted randomly to any direction, only the light proceeding to a specific direction can be diffracted when a general one-dimensional diffraction grating having a periodic refractive index distribution only in a specific direction is used, which does not greatly increase the light takeout efficiency However, by using diffraction grating having a two-dimensional refractive index distribution, the light proceeding to any direction can be diffracted, whereby the light take out efficiency is increased.

The diffraction grating may be provided between any of the layers on in any of the mediums (in the transparent substrate or in the transparent electrode), but it is preferably provided in the vicinity of the organic light emission layer where the light is emitted.

The period of the diffraction grating is preferably about ½ to 3 times of the wavelength of the light in the medium.

The array of the diffraction grating is preferably two-dimensionally repeated, for example, as in the shape of a square lattice, a triangular lattice, or a honeycomb lattice.

<<Light-condensing Sheet>>

In the organic EL device of the invention, luminance in a specified direction, for example, the front direction against the emitting plane of the device can be increased, for example, by processing to form a structure of a micro-lens array sheet on the light takeout side surface of the substrate or in combination with a so-called light-condensing sheet.

As an example of a micro-lens array, quadrangular pyramids 30 µm on a side and having a vertex angle of 90° are two-dimensionally arranged on the light takeout side surface of the substrate. The side of the quadrangular pyramids is preferably 10-100 µm. When the length of the side is shorter than the above range, the light is colored due to the effect of diffraction, and when it is longer than the above range, it becomes unfavorably thick.

As a light-condensing sheet, one practically applied for an LED backlight of a liquid crystal display is applicable. Examples of such a sheet include a brightness enhancing film (BEF) produced by SUMITOMO 3M Inc. As the shape of a prism sheet, one in which a triangle-shaped strip having a vertex angle of 90° and a pitch of 50 µm provided on a substrate, one having round apexes or one having a randomly changed pitch may be included.

In order to control an emission angle of emitting light from the light emitting device, a light diffusion plate or film may be used in combination with the light-condensing sheet. For example, a diffusion film (Light-Up) produced by KIMOTO Co., Ltd. can be used.

<<Preparation of Organic EL Device>>

For one example, the preparation of the organic EL device, which has the constitution, Anode/Hole injecting layer/Hole transporting layer/Light emission layer/Electron transporting layer/Electron injecting layer/Cathode, will be described.

A thin layer of a desired material for an electrode such as a material of the anode is formed on a suitable substrate by a deposition or sputtering method to prepare the anode, so that the thickness of the layer is not more than 1 µm, and preferably within the range of from 10 to 200 nm.

Then the hole injecting layer, the hole transporting layer, the light emission layer, the electron transporting layer and the electron injecting layer, which constitute the organic EL device, are formed on the resulting anode in that order as organic compound thin layers.

As methods for formation of these layers, there are a vapor deposition method and a wet process method (such as a spin coating method, a casting method, an ink jet method, and a printing method) as described above. A spin coating method, an ink jet method and a printing method are preferred, since a uniform layer can be formed and a pinhole is formed with difficulty, and an ink jet method is especially preferred.

In the invention, it is preferred that the light emission layer is formed via a coating method employing a liquid composition in which the organic metal complexes in the invention are dissolved or dispersed, and the coating method is preferably an ink-jet method.

As liquid media in which the organic metal complexes in the invention are dissolved or dispersed, employed may, for example, be ketones such as methyl ethyl ketone or cyclohexanone; aliphatic acid esters such as ethyl acetate; halogenated hydrocarbons such as dichlorobenzene; and organic solvents such as DMF or DMSO. Further, the dispersion can be carried out employing a dispersion method such as an ultrasonic wave dispersion method, a high shearing force dispersion method or a media dispersion method.

After these layers has been formed, a thin layer comprised of a material for a cathode is formed thereon to prepare a cathode, employing, for example, a deposition method or sputtering method to give a thickness of not more than 1 µm, and preferably from 50 to 200 nm. Thus, a desired organic EL device is obtained.

Further, the organic EL device can be prepared in the reverse order, in which the cathode, the electron injecting layer, the electron transporting layer, the light emission layer, the hole transporting layer, the hole injecting layer, and the anode are formed in that order. When a direct current voltage, a voltage of 2 to 40 V is applied to the thus obtained multicolor display, setting the anode as a + polarity and the cathode as a − polarity, light emission occurs. When voltage is applied with the reverse polarity, no current flows, and light is not emitted at all. When an alternating voltage is applied, light emission occurs only at the time when the polarity of the anode is "+", and that of the cathode is "−" The wave shape of the alternating current may be any one.

<<Use>>

The organic EL device of the invention can be used as a display device, a display, or various light emission sources. Examples of the light emission sources include an illuminating device (a home lamp or a room lamp in a carboxylic acid), a backlight for a watch or a liquid crystal, a light source for boarding advertisement, a signal device, a light source for a photo memory medium, a light source for an electrophotographic copier, a light source for an optical communication instrument, and a light source for an optical sensor, but are not limited thereto. Particularly, it is effectively used as a backlight for a liquid crystal or a light source for illumination.

In the organic EL device of the invention, patterning may be carried out through a metal mask or according to an ink-jet printing method The patterning may be carried out only in electrodes, in both electrodes and light emission layer, or in all the layers of the device. Further, the device can be also prepared according to a conventional method.

Color of light emitted from the organic EL device of the invention or the compounds in the invention is specified in such a manner that results determined by a spectral radiance luminance meter CS-1000 (produced by Konica Minolta Sensing Co., Ltd.) are applied to the CIE chromaticity coordinates in FIG. 4.4.16 on page 108 of "Shinpen Shikisai Kagaku Handbook (edited by The Color Science Association of Japan, University of Tokyo Press, 1985).

When the organic EL device of the invention is a white light device, "white" means that when front luminance of a 2° viewing angle is determined via the above method, chromaticity in the CIE 1931 Chromaticity System at 1,000 Cd/m² is in the range of X=0.33±0.07 and Y=0.33±0.07.

EXAMPLES

The present invention will be explained in the following examples, but is not limited thereto. Compounds used in the examples will be shown below.

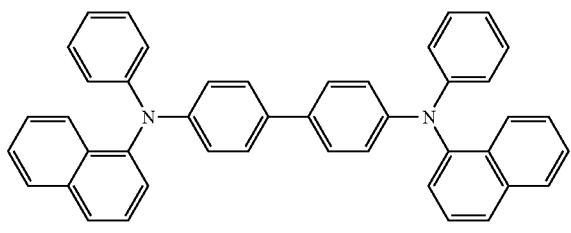

α-NPD

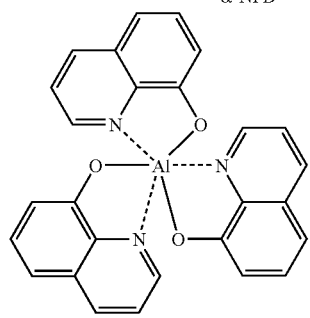

Alq3

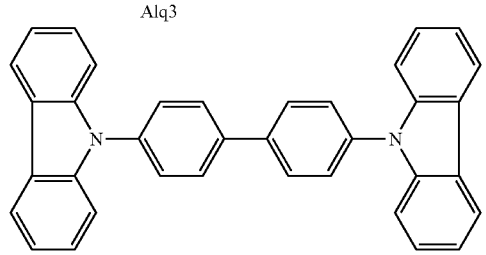

CBP

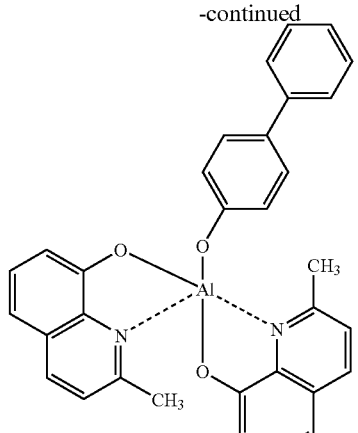

Balq

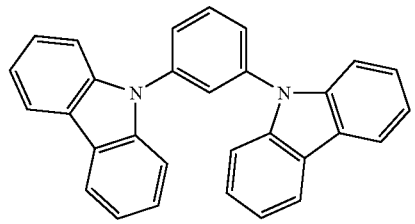

m-CP

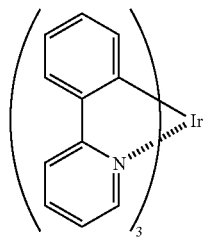

Ir(ppy)3

Example 1

<<Synthesis of Organic EL Device Material H-1>>

Organic EL device material H-1 of the intention was synthesized according to the following reaction scheme:

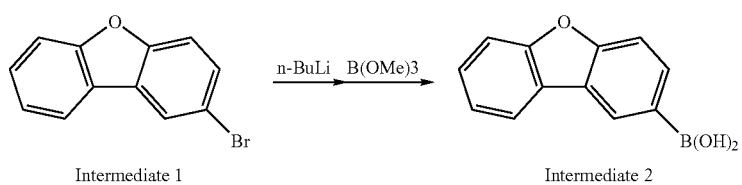

Intermediate 1           Intermediate 2

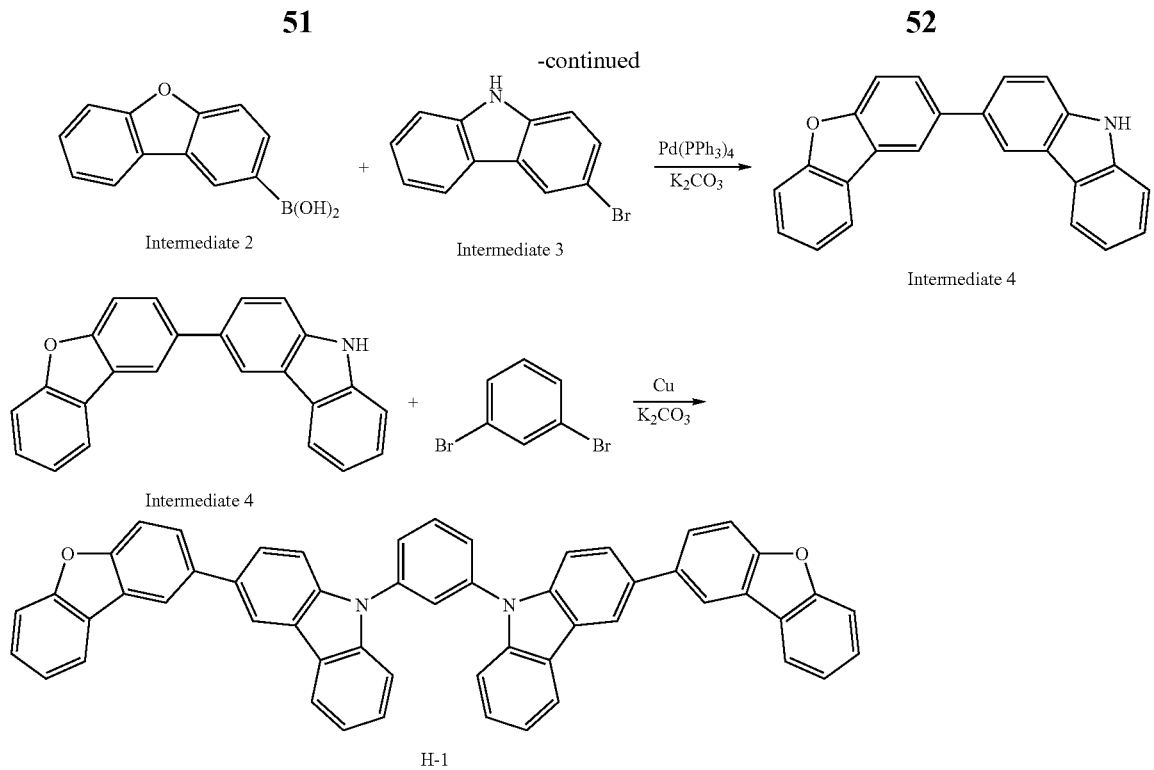

(Synthesis of Intermediate 2)

Intermediate 1 of 24.7 g were placed in a 500 ml three-necked flask and 300 ml of THF (anhydrous) were incorporated therein under nitrogen atmosphere employing a syringe. The resulting mixture was cooled with acetone/dry ice, and 76.2 ml of n-BuLi (1.6 mol/L) was dropwise added thereto at −60° C. The resulting mixture was stirred at 60° C. for 1 hour, then dropwise added with a mixture solution of 24.0 g of trimethoxyborane and 30 ml of THF (anhydrous) heated to room temperature, and then stirred for 2 hours.

The resulting reaction solution was added with 150 ml of an aqueous 10% hydrochloric acid solution, washed with water three times employing a separating-funnel and dried over anhydrous $MgSO_4$.

The dried solution was filtered off and the filtrate was concentrated to obtain a solid product. The resulting solid product was washed with hexane. Thus, 10.5 g of Intermediate 2 were obtained.

(Synthesis of Intermediate 4)

Intermediate 2 of 9.5 g and 10 g of Intermediate 3 were placed in a 500 ml three-necked flask and 250 ml of THF (anhydrous) were incorporated therein under nitrogen atmosphere. The resulting mixture was added with a solution in which 8.5 g of $K_2CO_3$ were dissolved in 75 ml water and then with 4.5 g of $Pd(PPh_3)_4$, and reacted under reflux for 10 hours. The resulting reaction solution was washed with water three times employing a separating funnel and dried over $MgSO_4$. The dried solution was filtered off and the filtrate was concentrated to obtain a solid product. The resulting solid product was purified according to silica gel chromatography employing a hexane/ethyl acetate (=8/1) mixture solvent as an eluting solvent. Thus, 5.6 g of Intermediate 4 were obtained.

(Synthesis of H-1)

Intermediate 4 of 3.6 g, 1.2 g of m-dibromobenzene, 150 ml of dimethylacetoamide, 0.85 g of copper powder and 2.1 g of $K_2CO_3$ were introduced in a 300 ml three-necked flask, and reacted at 150° C. for 8 hours. After that, the resulting reaction solution was added with water and ethyl acetate, and the organic-phase thereof was washed with water three times employing a separating funnel and dried over $MgSO_4$. The dried solution was filtered off and the filtrate was concentrated to obtain a solid product. The resulting solid product was purified according to silica gel chromatography employing a hexane/ethyl acetate (=10/1) mixture solvent as an eluting solvent. Thus, 1.1 g of H-1 were obtained.

The chemical structure of the compound was identified according to $^1$H-NMR spectra. The spectra measurement conditions and information from the spectra are shown below.

$^1$H-NMR (400 MHz, $CDCl_3$)

8.44 (2H, d), 8.26 (4H, m), 8.05 (2H, d), 7.92 (2H, m), 7.79 (6H, m), 7.68 (4H, d), 7.51 (4H, d), 7.50 (4H, m), 7.38 (4H, m)

Example 2

<<Preparation of Organic EL Devices 1-1 Through 1-15>>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 200 mg of m-CP as a host compound were put in a second resistive heating molybdenum boat, 200 mg of Balq were put in a third resistive heating molybdenum boat, 100 mg of 1-1 were put in a fourth resistive heating molybdenum boat, and 200 mg of $Alq_3$ were put in a fifth resistive heating molybdenum boat. The resulting boats were placed in the vacuum deposition apparatus.

Subsequently, pressure in the vacuum tank was reduced to $4\times10^{-4}$ Pa. Then, the boat carrying α-NPD being heated by supplying an electric current to the boat, α-NPD was deposited onto the transparent substrate at a depositing speed of 0.1 nm/sec to form a hole transporting layer with a thickness of 40 nm. After that, the boat carrying m-CP and the boat carrying 1-1 being heated by supplying an electric current to both boats, m-CP at a depositing speed of 0.2 nm/sec and 1-1 at a depositing speed of 0.012 nm/sec were co-deposited onto the resulting hole transporting layer to form a light emission layer with a thickness of 40 nm. The temperature of the substrate at the time of the deposition was room temperature. Subsequently, the boat carrying Balq being heated by supplying an electric current to the boat, Balq was deposited onto the resulting light emission layer at a depositing speed of 0.1 nm/sec to form a hole inhibiting layer with a thickness of 10 nm. Further, the boat carrying $Alq_3$ being heated by supplying an electric current to the boat, $Alq_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a 110 nm thick aluminum layer were deposited on the resulting material to form a cathode. Thus, organic EL device 1-1 was prepared.

The non-light-emitting face of each of the organic EL devices was covered with a glass case, and a sealing glass plate having a thickness of 300 μm was piled as a sealing substrate on the cathode so as to be contacted with the transparent substrate using, as a sealing material, an epoxy type photocurable adhesive, Laxtruck LC0629B manufactured by Toa Gousei Co., Ltd., and then the adhesive was cured by UV ray irradiation from the glass plate to seal. Thus, illuminating devices as shown in FIG. 1 or 2 were prepared and evaluated.

Figure 2:
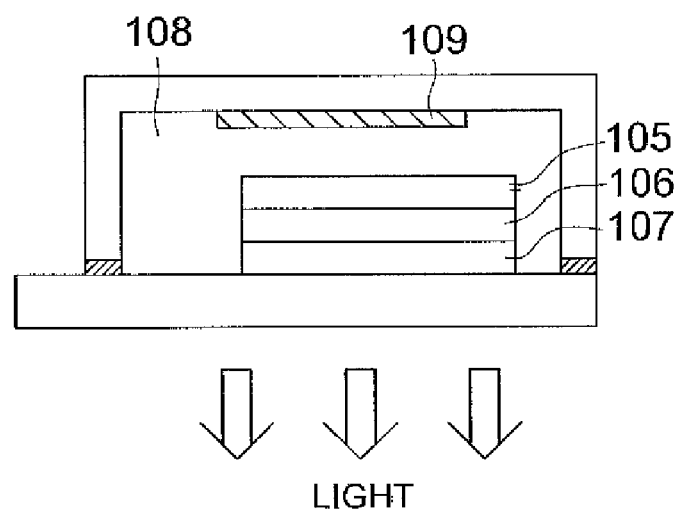
FIG. 2 is a sectional view of an illuminating device.

FIG. 1 shows a schematic drawing of an illuminating device.

Organic EL device 101 is covered with a glass cover 102. (The sealing work in the glass cover was carried out in a globe box filled with nitrogen gas (highly purified nitrogen gas having a purity of 99.999% or more) so that the organic EL device 101 did not contact air.) FIG. 2 is a sectional view of an illuminating device. In FIG. 2, Numerical No. 105 is a cathode, numerical No. 106 is an organic EL layer, and numerical No. 107 is a glass substrate with a transparent electrode. In the inside of the glass cover 102, nitrogen gas 108 is introduced and a water-trapping agent 109 is placed.

<<Preparation of Organic EL Devices 1-2 Through 1-20>>

Organic EL devices 1-2 through 1-20 were prepared in the same manner as organic EL device 1-1 above, except that the emission host and the emission dopant were changed to those as shown in Table 1.

<<Evaluation Of Organic EL Devices 1-1 Through 1-20>>

The organic EL devices 1-1 through 1-20 obtained above were evaluated according to the following method. The results are shown in Table 1.

(External Quantum Efficiency)

Electric current of 2.5 mA/cm² was supplied to each sample at 23° C. in an atmosphere of a dry nitrogen gas, external quantum efficiency (%) of each sample was measured. The external quantum efficiency (%) was measured employing a spectral radiance luminance meter CS-1000 (produced by Minolta Co., Ltd.).

External quantum efficiency in Table 1 was expressed by a relative value when external quantum efficiency of organic EL device 1-15 was set at 100.

(Lifetime)

When electric current of 2.5 mA/cm² was supplied to each sample, time required to reduce to half of luminance (initial luminance) at the beginning of emission was determined as a half-life period ($\tau^{0.5}$) and evaluated as a measure of lifetime. The Luminance was measured employing a spectral radiance luminance meter CS-1000 (produced by Konica Minolta Sensing Co., Ltd.).

The results are shown in Table 1. Lifetime in Table 1 was expressed by a relative value when lifetime of organic EL device 1-15 was set at 100.

TABLE 1

| Organic EL Device No. | Guest Compound | Host Compound | External Quantum Efficiency | Lifetime | Remarks |
|---|---|---|---|---|---|
| 1-1 | 1-1 | m-CP | 100 | 100 | Comp. |
| 1-2 | 1-2 | m-CP | 98 | 101 | Comp. |
| 1-3 | 1-5 | m-CP | 105 | 90 | Comp. |
| 1-4 | 1-1 | H-1 | 130 | 140 | Inv. |
| 1-5 | 1-2 | H-1 | 126 | 145 | Inv. |
| 1-6 | 1-5 | H-1 | 122 | 134 | Inv. |
| 1-7 | 1-1 | H-2 | 119 | 120 | Inv. |
| 1-8 | 1-2 | H-2 | 110 | 119 | Inv. |
| 1-9 | 1-1 | H-3 | 128 | 136 | Inv. |
| 1-10 | 1-2 | H-3 | 125 | 138 | Inv. |
| 1-11 | 1-1 | H-5 | 125 | 121 | Inv. |
| 1-12 | 1-2 | H-5 | 123 | 123 | Inv. |
| 1-13 | 1-1 | H-12 | 130 | 138 | Inv. |
| 1-14 | 1-2 | H-12 | 126 | 135 | Inv. |
| 1-15 | 1-20 | H-1 | 120 | 120 | Inv. |
| 1-16 | 1-20 | H-3 | 117 | 115 | Inv. |
| 1-17 | 1-31 | H-1 | 119 | 123 | Inv. |
| 1-18 | 1-31 | H-3 | 120 | 120 | Inv. |
| 1-19 | 1-20 | m-CP | 99 | 98 | Comp. |
| 1-20 | 1-31 | m-CP | 97 | 93 | Comp. |

Comp.: Comparative,
Inv.: Inventive

As is apparent from Table 1 above, inventive organic EL devices provide high emission efficiency and long lifetime as compared to comparative organic EL devices.

Example 2

<<Preparation of Organic EL Device 2-1>>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 200 mg of CBP as a host compound were put in a second resistive heating molybdenum boat, 200 mg of Balq were put in a third resistive heating molybdenum boat, 100 mg of Ir $(ppy)_3$ were put in a fourth resistive heating molybdenum-boat, and 200 mg of $Alq_3$ were put in a fifth resistive heating molybdenum boat. The resulting boats were placed in the vacuum deposition apparatus.

Subsequently, pressure in the vacuum tank was reduced to $4\times10^{-4}$ Pa. Then, the boat carrying α-NPD being heated by supplying an electric current to the boat, α-NPD was deposited onto the transparent substrate at a depositing speed of 0.1 nm/sec to form a hole transporting layer with a thickness of 40 nm.

After that, the boat carrying CBP and the boat carrying Ir-1 being heated by supplying an electric current to both boats, m-CP at a depositing speed of 0.2 nm/sec and 1-1 at a depositing speed of 0.012 nm/sec were co-deposited onto the resulting hole transporting layer to form a light emission layer with a thickness of 40 nm. The temperature of the substrate at the time of the deposition was room temperature. Subsequently, the boat carrying Balq being heated by supplying an electric current to the boat, Balq was deposited onto the resulting light emission layer at a depositing speed of 0.1 nm/sec to form a hole inhibiting layer with a thickness of 10 nm. Further, the boat carrying $Alq_3$ being heated by supplying an electric current to the boat, $Alq_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a 110 nm thick aluminum layer were deposited on the resulting material to form a cathode. Thus, organic EL device 2-1 was prepared.

The resulting device was sealed employing a sealing having the same structure as Example 1 in the same manner as in Example 1. Thus, a flat lamp was obtained.

<<Preparation of Organic EL Devices 2-2 Through 2-18>>

Organic EL devices 2-2 through 1-15 were prepared in the same manner as organic EL device 2-1 above, except that the emission host was changed to those as shown in Table 2.

The organic EL devices 2-1 through 2-15 obtained above were evaluated in the same manner as in Example 1. The results are shown in Table 2. External quantum efficiency and lifetime were expressed by a relative value when external quantum efficiency and lifetime of organic EL device 2-1 were set at 100, respectively.

TABLE 2

| Organic EL Device No. | Host Compound | External Quantum Efficiency | Lifetime | Remarks |
|---|---|---|---|---|
| 2-1 | CBP | 100 | 100 | Comp. |
| 2-2 | H-1 | 120 | 126 | Inv. |
| 2-3 | H-2 | 115 | 110 | Inv. |
| 2-4 | H-3 | 128 | 122 | Inv. |
| 2-5 | H-5 | 109 | 111 | Inv. |
| 2-6 | H-12 | 110 | 121 | Inv. |
| 2-7 | H-13 | 108 | 118 | Inv. |

Comp.: Comparative,
Inv.; Inventive

As is apparent from Table 2 above, inventive organic EL devices provide high emission efficiency and long emission lifetime as compared to comparative organic EL device.

Example 3

<<Preparation of Organic EL Device 3-1>>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 100 mg of m-CP as an electron inhibiting compound were put in a second resistive heating molybdenum boat, 200 mg of CBP as a host compound were put in a third resistive heating molybdenum boat, 200 mg of Balq were put in a fourth resistive heating molybdenum boat, 100 mg of 1-1 were put in a fifth resistive heating molybdenum boat, and 200 mg of $Alq_3$ were put in a sixth resistive heating molybdenum boat. The resulting boats were placed in the vacuum deposition apparatus.

Subsequently, pressure in the vacuum tank was reduced to $4\times10^{-4}$ Pa. Then, the boat carrying α-NPD being heated by supplying an electric current to the boat, α-NPD was deposited onto the transparent substrate at a depositing speed of 0.1 nm/sec to form a hole transporting layer with a thickness of 40 nm. Then, the boat carrying m-CP being heated by supplying an electric current to the boat, m-CP was deposited onto the resulting hole transporting layer at a depositing speed of 0.1 nm/sec to form an electron inhibiting layer with a thickness of 10 nm. After that, the boat carrying m-CP and the boat carrying 1-1 being heated by supplying an electric current to both boats, m-CP at a depositing speed of 0.2 nm/sec and 1-1 at a depositing speed of 0.012 nm/sec were co-deposited onto the resulting electron inhibiting layer to form a light emission layer with a thickness of 40 nm. The temperature of the substrate at the time of the deposition was room temperature. Subsequently, the boat carrying $Balq_3$ being heated by supplying an electric current to the boat, $Balq_3$ was deposited onto the resulting light emission layer at a depositing speed of 0.1 nm/sec to form a hole inhibiting layer with a thickness of 10 nm. Further, the boat carrying $Alq_3$ being heated by supplying an electric current to the boat, $Alq_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a 110 nm thick aluminum layer were deposited on the resulting material to form a cathode. Thus, organic EL device 3-1 was prepared.

<<Preparation of Organic EL Devices 3-2 Through 3-9>>

Organic EL devices 3-2 through 3-10 were prepared in the same manner as organic EL device 3-1 above, except that CBP used as a host compound in the light emission layer was changed to those as shown in Table 2 and CBP used in the electron inhibiting layer was changed to those as shown in Table 3.

<<Evaluation of Organic EL Devices 3-1 Through 3-9>>

The organic EL devices 3-1 through 3-9 obtained above were evaluated. The results are shown in Table 3.

TABLE 3

| Organic EL Device No. | Electron Inhibiting Layer | Host Compound | External Quantum Efficiency | Lifetime | Remarks |
|---|---|---|---|---|---|
| 3-1 | m-CP | m-CP | 100 | 100 | Comp. |
| 3-2 | H-1 | H-1 | 128 | 131 | Inv. |
| 3-3 | H-2 | H-2 | 120 | 115 | Inv. |
| 3-4 | H-3 | H-3 | 126 | 128 | Inv. |
| 3-5 | H-5 | H-5 | 113 | 115 | Inv. |
| 3-6 | H-2 | H-1 | 114 | 120 | Inv. |
| 3-7 | H-3 | H-1 | 128 | 127 | Inv. |
| 3-8 | H-5 | H-1 | 113 | 115 | Inv. |
| 3-9 | H-1 | m-CP | 105 | 108 | Inv. |

Comp.: Comparative,
Inv.: Inventive

As is apparent from Table 3 above, inventive organic EL devices provide high emission efficiency and long emission lifetime as compared to comparative organic EL device.

Example 4

<<Preparation of Organic EL Devices 4-1 Through 4-5>>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 200 mg of m-CP as a host compound were put in a second resistive heating molybdenum boat, 200 mg of Balq were put in a third resistive heating molybdenum boat, 100 mg of 1-1 were put in a fourth resistive heating molybdenum boat, and 200 mg of Alq$_3$ were put in a fifth resistive heating molybdenum boat. The resulting boats were placed in the vacuum deposition apparatus.

Subsequently, pressure in the vacuum tank was reduced to 4×10$^{-4}$ Pa. Then, the boat carrying α-NPD being heated by supplying an electric current to the boat, α-NPD was deposited onto the transparent substrate at a depositing speed of 0.1 nm/sec to form a hole transporting layer with a thickness of 40 nm. After that, the boat carrying m-CP being heated by supplying an electric current to the boat, m-CP at a depositing speed of 0.1 nm/sec was deposited onto the resulting hole transporting layer to form an electron inhibiting with a thickness of 10 nm. Further, the boat carrying m-CP and the boat carrying 1-1 being heated by supplying an electric current to both boats, m-CP at a depositing speed of 0.2 nm/sec and 1-1 at a depositing speed of 0.012 nm/sec were co-deposited onto the resulting electron inhibiting layer to form a light emission layer with a thickness of 40 nm. The temperature of the substrate at the time of the deposition was room temperature. Subsequently, the boat carrying Balq being heated by supplying an electric current to the boat, Balq was deposited onto the resulting light emission layer at a depositing speed of 0.1 nm/sec to form a hole inhibiting layer with a thickness of 10 nm. Further, the boat carrying Alq$_3$ being heated by supplying an electric current to the boat, Alq$_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a 110 nm thick aluminum layer were deposited on the resulting material to form a cathode. Thus, organic EL device 4-1 was prepared.

<<Preparation of Organic EL Devices 4-2 Through 4-5>>

Organic EL devices 4-2 through 4-5 were prepared in the same manner as organic EL device 4-1 above, except that m-CP used as a host compound in the light emission layer was changed to those as shown in Table 4 and Balq used in the hole inhibiting layer was changed to those as shown in Table 4.

<Evaluation of Organic EL Devices 4-1 Through 4-5>>

The organic EL devices 4-1 through 4-5 obtained above were evaluated in the same manner as in Example 1. The results are shown in Table 4.

TABLE 4

| Organic EL Device No. | Host Compound | Hole Inhibiting Layer | External Quantum Efficiency | Lifetime | Remarks |
| --- | --- | --- | --- | --- | --- |
| 4-1 | m-CP | Balq | 100 | 100 | Comp. |
| 4-2 | H-1 | H-1 | 120 | 105 | Inv. |
| 4-3 | H-3 | H-3 | 120 | 106 | Inv. |
| 4-4 | H-1 | H-3 | 118 | 110 | Inv. |
| 4-5 | m-CP | H-1 | 110 | 105 | Inv. |

Comp.: Comparative,
Inv.: Inventive

As is apparent from Table 4 above, inventive organic EL devices provide high emission efficiency and long emission lifetime as compared to comparative organic EL devices.

Example 5

An electrode pattern of 20 mm×20 mm was formed on the transparent electrode substrate of Example 1. An α-NPD layer with a thickness of 50 nm was formed as a hole injecting/transporting layer on the resulting electrode.

After that, electric current was supplied to the boat carrying Compound 1, the boat carrying 1-1 and a boat carrying Ir-9, respectively, so that the deposition speed ratio of emission host Compound remission dopant 1-1 and Ir-9 was 100:5:0.6. Thus, whereby a light emission layer with a thickness of 30 nm was formed as a deposition layer.

Subsequently, a hole inhibiting layer of Balq with a thickness of 10 nm was formed and then, an electron transporting layer of Alq$_3$ with a thickness of 40 nm was formed Successively, the vacuum tank was opened, a square mask made of stainless steel having the same shape as the transparent electrode and having a hole was placed on the electron injecting layer. After that, a 0.5 nm thick lithium fluoride layer was deposited to form a cathode buffering layer and a 110 nm thick aluminum layer was deposited to form a cathode.

The resulting device was sealed employing a sealing can having the same structure as Example 1 in the same manner as in Example 1. Thus, a flat lamp was obtained.

Electric current was applied to the resulting flat lamp, and almost white light was generated, whereby it was found that it was possible to employ it as an illuminating device. It was also found that white light was emitted in a flat lamp in which the emission host is replaced with other inventive compounds.

The invention claimed is:

1. An organic electroluminescent device comprising a substrate, and provided thereon, an anode and a cathode, at least one organic layer being provided between the anode and the cathode, wherein the at least one organic layer contains a compound represented by formula (1), Formula (1)

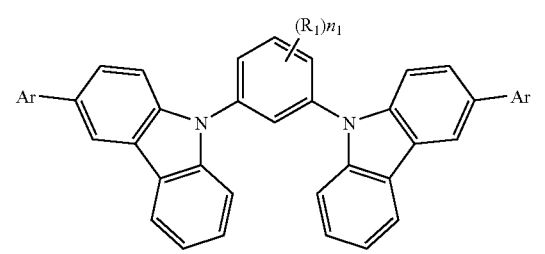

wherein R₁ represents a hydrogen atom, an alkyl group, an cycloalkyl group, an alkenyl group, an alkynyl group, an aromatic hydrocarbon group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amido group, a carbamoyl group, a ureido group, a sulfinyl group, an alkylsulfonyl group, an arylsulfonyl group, an amino group, a cyano group, an nitro group, a hydroxyl group, a mercapto group or a silyl group; Ar represents an aromatic hydrocarbon group or an aromatic heterocyclic group; and n₁ represents an integer of from 0 to 4.

2. The organic electroluminescent device of claim 1, wherein Ar in formula (1) represents an aromatic heterocyclic group.

3. The organic electroluminescent device of claim 1, wherein the organic layer comprises at least one electron inhibiting layer and the electron inhibiting layer contains a compound represented by formula (1).

4. The organic electroluminescent device of claim 1, wherein the organic layer comprises at least one hole inhibiting layer and the hole inhibiting layer contains a compound represented by formula (1).

5. The organic electroluminescent device of claim 1, wherein the organic electroluminescent device emits a white light.

6. A display comprising the organic electroluminescent device of claim 1.

7. An organic electroluminescent device comprising the compound represented by formula (1) of claim 1.

8. The organic electroluminescent device material of claim 1, wherein in formula (1), R₁ represents a hydrogen atom or an aromatic hydrocarbon group.

9. The organic electroluminescent device of claim 1, wherein the compound represented by formula (1) is a compound represented by formula (2), famoyl group, an acyl group, an aryloxy group, an amido group, a carbamoyl group, a ureido group, a sulfinyl group, an alkylsulfonyl group, an arylsulfonyl group, an amino group, a cyano group, an nitro group, a hydroxyl group, a mercapto group or a silyl group; X represents O, S or —N(Ra)— (in which Ra represents a hydrogen atom, an alkyl group, an alkenyl group, an alkynyl group, or a cycloalkyl group); R₂ through R₅ independently represent a hydrogen atom or a substituent; n₁, n₃ and n₅ independently represent an integer of from 0 to 4; and n₂ and n₄ independently represent an integer of from 0 to 3.

10. The organic electroluminescent device of claim 9, wherein X in formula (2) represents O or S.

11. The organic electroluminescent device of claim 9, wherein the organic layer comprises at least one light emission layer comprises at least one light emission layer and the light emission layer contains a compound represented by formula (2).

12. The organic electroluminescent device of claim 9, wherein the organic layer comprises at least one electron inhibiting layer and the electron inhibiting layer contains a compound represented by formula (2).

13. The organic electroluminescent device of claim 9, wherein the organic layer comprises at least one hold inhibiting layer and the hole inhibiting layer contains a compound represented by formula (2).

14. An organic electroluminescent device material a compound represented by formula (2) of claim 9.

15. The organic electroluminescent device of claim 1, wherein the organic layer comprises at least one light emission layer and the light emission layer contains a compound represented by formula (1).

16. The organic electroluminescent device of claim 15, wherein the light emission layer contains a phosphorescence emission dopant.

17. The organic electroluminescent device of claim 16, wherein the phosphorescence emission dopant has a 0-0 band of not more than 485 nm.

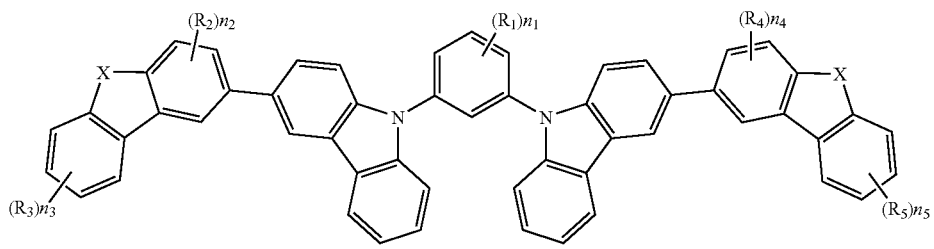

Formula (2)

wherein R₁ represents a hydrogen atom, an alkyl group, an cycloalkyl group, an alkenyl group, an alkynyl group, an aromatic hydrocarbon group, an alkoxy group, a cycloalkoxy group, an aryloxy group, an alkylthio group, a cycloalkylthio group, an arylthio group, an alkoxycarbonyl group, an aryloxycarbonyl group, a sul- 18. An illuminating device comprising the organic electroluminescent device of claim 1.

19. A display comprising the illuminating device of claim 18 and a liquid crystal device as a displaying means.

* * * * *